United States Patent
Ishida

(10) Patent No.: US 12,138,406 B2
(45) Date of Patent: Nov. 12, 2024

(54) CATHETER, NEEDLE, AND GUIDEWIRE ASSEMBLY

(71) Applicant: TERUMO KABUSHIKI KAISHA, Tokyo (JP)

(72) Inventor: Masahiro Ishida, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 685 days.

(21) Appl. No.: 17/025,640

(22) Filed: Sep. 18, 2020

(65) Prior Publication Data

US 2021/0001092 A1 Jan. 7, 2021

Related U.S. Application Data

(63) Continuation of application No. PCT/JP2019/013494, filed on Mar. 28, 2019.

(30) Foreign Application Priority Data

Mar. 29, 2018 (JP) ................................. 2018-064988

(51) Int. Cl.
*A61M 25/06* (2006.01)
*A61M 25/00* (2006.01)
(Continued)

(52) U.S. Cl.
CPC ...... *A61M 25/065* (2013.01); *A61M 25/0147* (2013.01); *A61M 25/09* (2013.01); *A61M 2025/0062* (2013.01)

(58) Field of Classification Search
CPC ............ A61M 25/0067; A61M 25/001; A61M 25/008; A61M 25/0069; A61M 25/0068;
(Continued)

(56) References Cited

U.S. PATENT DOCUMENTS 4,917,102 A * 4/1990 Miller ............. A61M 25/09025
600/585
5,664,580 A * 9/1997 Erickson ............... A61M 25/09
128/877
(Continued)

FOREIGN PATENT DOCUMENTS

EP 2005988 B1 * 3/2016 ............ A61M 25/09
JP 2001-340466 A 12/2001
(Continued)

OTHER PUBLICATIONS

Mateiral data for gold, www.matweb.com/search/DataSheet.aspx?MatGUID=d2a2119a08904a0fa706e9408cddb88e (accessed Apr. 17, 2024) (Year: 2024).*

(Continued)

*Primary Examiner* — Jason E Flick
*Assistant Examiner* — Adam J. Cermak
(74) *Attorney, Agent, or Firm* — Foley & Lardner LLP

(57) ABSTRACT

A catheter assembly includes: a catheter including a distal end portion, and a body portion that is continuous with a proximal end of the distal end portion and extends along an axial direction; a hollow inner needle that has a needle tip and is removably inserted into the catheter; and a guide wire that is inserted into the inner needle so as to be movable back and forth and that is deliverable from the needle tip. The distal end portion of the catheter includes a constituent portion that is harder than, has a higher lubricity than, or has a higher elasticity than the body portion at at least a part of a surface of the distal end portion.

13 Claims, 12 Drawing Sheets

(51) Int. Cl.
*A61M 25/01* (2006.01)
*A61M 25/09* (2006.01)
(58) Field of Classification Search
CPC ............ A61M 25/0053; A61M 25/005; A61M 25/0045; A61M 25/0023; A61M 2025/1093; A61M 2025/09175; A61M 2025/0081; A61M 2205/0216
See application file for complete search history.

(56) References Cited

U.S. PATENT DOCUMENTS

| | | | | |
|---|---|---|---|---|
| 5,700,253 | A * | 12/1997 | Parker | A61M 25/0012 604/524 |
| 5,769,830 | A * | 6/1998 | Parker | A61M 25/0069 604/528 |
| 6,183,420 | B1 * | 2/2001 | Douk | A61M 25/09 600/585 |
| 6,776,788 | B1 * | 8/2004 | Klint | A61B 17/12172 606/200 |
| 7,322,944 | B2 * | 1/2008 | Osawa et al. | A61M 25/09 128/877 |
| 7,909,779 | B2 * | 3/2011 | Shimogami | A61M 25/0012 72/135 |
| 7,985,213 | B2 * | 7/2011 | Parker | A61M 25/005 604/526 |
| 8,540,695 | B2 * | 9/2013 | Shimogami | A61M 25/005 604/525 |
| 8,814,890 | B2 * | 8/2014 | Miyata | A61M 25/0082 606/159 |
| 9,162,037 | B2 * | 10/2015 | Belson et al. | A61M 25/005 604/526 |
| 9,522,254 | B2 * | 12/2016 | Belson | A61M 25/09 |
| 10,220,191 | B2 * | 3/2019 | Belson et al. | A61M 25/001 |
| 11,096,703 | B2 * | 8/2021 | Panian | A61M 25/0105 |
| 11,369,774 | B2 * | 6/2022 | Hori | A61M 25/008 |
| 2009/0018525 | A1 * | 1/2009 | Waite | A61M 25/008 604/104 |
| 2011/0106056 | A1 * | 5/2011 | Hatano | A61M 25/0052 604/527 |
| 2011/0196315 | A1 * | 8/2011 | Chappel | A61M 25/0069 604/264 |
| 2011/0245775 | A1 * | 10/2011 | Tekulve | A61M 25/0045 264/171.12 |
| 2012/0310213 | A1 * | 12/2012 | Kronfeld | A61M 25/001 604/529 |
| 2015/0231360 | A1 * | 8/2015 | Watanabe et al. | A61M 25/0012 72/135 |
| 2015/0273182 | A1 * | 10/2015 | Watanabe | A61M 25/0069 604/527 |
| 2016/0151078 | A1 * | 6/2016 | Kanazawa | A61M 25/001 606/159 |
| 2016/0279383 | A1 * | 9/2016 | Kanazawa | A61M 25/001 |
| 2016/0331938 | A1 * | 11/2016 | Blanchard | A61M 25/0618 |
| 2017/0072165 | A1 * | 3/2017 | Lim et al. | A61M 25/005 |
| 2017/0113018 | A1 * | 4/2017 | Shimizu | A61M 25/005 |
| 2018/0056037 | A1 * | 3/2018 | Shimizu | A61M 25/0052 |
| 2019/0167305 | A1 * | 6/2019 | Pedersen | A61B 17/3468 |
| 2020/0129730 | A1 * | 4/2020 | Ishikawa | A61M 25/0068 |
| 2020/0353216 | A1 * | 11/2020 | Hori | A61M 25/008 |

FOREIGN PATENT DOCUMENTS

| | | | | |
|---|---|---|---|---|
| JP | 2005-169012 | A | | 6/2005 |
| JP | 2007244492 | A * | 9/2007 | |
| JP | 2009-500129 | A | | 1/2009 |
| JP | 2013-518691 | A | | 5/2013 |
| JP | 2014-236863 | A | | 12/2014 |
| JP | 2015-208425 | A | | 11/2015 |
| JP | 2016152907 | A * | 8/2016 | ........ A61M 25/0012 |
| JP | 2016-214391 | A | | 12/2016 |
| JP | 2017-148837 | A | | 8/2017 |
| JP | 2017-164423 | A | | 9/2017 |
| JP | 2019037572 | A * | 3/2019 | ............ A61M 25/00 |
| WO | WO-9426337 | A1 * | 11/1994 | ........... A61L 31/022 |
| WO | WO-9711738 | A1 * | 4/1997 | ........... A61M 25/09 |
| WO | WO-9732518 | A1 * | 9/1997 | ........... A61B 5/0215 |
| WO | WO-9919017 | A1 * | 4/1999 | ............. A61M 25/09 |
| WO | WO-2012158152 | A1 * | 11/2012 | ........ A61B 1/00087 |
| WO | WO-2019026220 | A1 * | 2/2019 | ........... A61M 25/001 |
| WO | WO-2021090821 | A1 * | 5/2021 | ........ A61M 25/0045 |

OTHER PUBLICATIONS

Overview of materials for thermoplastic polyurethane, elastomer, polyester grade, www.matweb.com/search/DataSheet.aspx?MatGUID= 9f5318a1f93b403bbd5748abec70fac1 (accessed Apr. 17, 2024) (Year: 2024).*

International Searching Authority, "Written Opinion," issued in connection with International Patent Application No. PCT/JP2019/013494, dated Jun. 18, 2019.

International Searching Authority, "International Search Report," issued in connection with International Patent Application No. PCT/JP2019/013494, dated Jun. 18, 2019.

Japanese Office Action issued in connection with JP Appl. Ser. No. 2020-509297 dated Oct. 25, 2022.

* cited by examiner

CATHETER, NEEDLE, AND GUIDEWIRE ASSEMBLY

CROSS-REFERENCE TO RELATED APPLICATIONS

This application is a bypass continuation of PCT Application No. PCT/JP2019/013494, filed on Mar. 28, 2019, which claims priority to Japanese Application No. 2018-064988, filed on Mar. 29, 2018. The contents of these applications are hereby incorporated by reference in their entireties.

BACKGROUND

The present disclosure relates to a catheter assembly configured to deliver a guide wire to guide insertion of a catheter.

A catheter assembly having a multi-structure needle in which an inner needle is inserted into a catheter is disclosed in U.S. Pat. No. 9,162,037 A. When the catheter is inserted into a blood vessel of a patient, this catheter assembly delivers a guide wire in advance from a needle tip of the inner needle such that the guide wire guides insertion of the catheter.

In particular, the guide wire disclosed in U.S. Pat. No. 9,162,037 A has a distal end portion formed into a curved portion that is shaped into a coil shape in a natural state. The curved portion is wound into a coil shape to form a rounded outer shape while being delivered from the inner needle, and thus, can make it difficult to be caught on a blood vessel wall, and can thereby suppress damage to the blood vessel wall.

SUMMARY

However, the guide wire configured as described above is likely to come into contact with the catheter and damage a distal end portion of the catheter while being curved into a coil at the time of delivering the guide wire. For example, the damage to the distal end portion of the catheter includes a case in which a distal end of the guide wire pierces or scratches the catheter.

Further, there is a case in which the inside of the catheter comes into contact with the guide wire so that the distal end of the catheter flips and is damaged at the time of advancing the catheter. Incidentally, even if a guide wire is formed in a shape having no curved portion (for example, extends linearly), a distal end of a guide wire may come into contact with a blood vessel and be bent back toward a catheter, so that there is a possibility that similar phenomena and similar damage to the catheter is caused.

Certain embodiments of the present invention have been developed in view of the above circumstances, and an object of certain embodiments is to provide a catheter assembly that can favorably suppressing damage to a catheter caused by a guide wire even with a configuration in which the guide wire is delivered in advance.

According to one embodiment, a catheter assembly includes: a catheter having a distal end portion and a body portion that is continuous with a proximal end of the distal end portion and extends along an axial direction; a hollow inner needle that has a needle tip and is removably inserted into the catheter; and a guide wire that is inserted into the inner needle so as to be movable back and forth and is delivered from the needle tip, the distal end portion of the catheter having a constituent portion that is harder than the body portion on at least a part of a surface of the distal end portion.

Further, a configuration in which the guide wire has a curved portion at a distal portion delivered from the inner needle may be adopted.

Further, the constituent portion may be provided on an outer peripheral surface of the distal end portion of the catheter.

Furthermore, the distal end portion of the catheter may have a tapered outer peripheral surface that tapers in a distal direction, and the constituent portion may be provided in a region including the tapered outer peripheral surface.

Furthermore, the distal end portion of the catheter may have a tapered outer peripheral surface that tapers in a distal direction, and the constituent portion may be provided on an outer peripheral surface proximal of the tapered outer peripheral surface.

Alternatively, the constituent portion may be provided on an inner peripheral surface of the distal end portion of the catheter.

Furthermore, the constituent portion may be provided at a most distal end of the distal end portion of the catheter.

In the catheter, it is preferable that another constituent portion forming a part of the distal end portion other than a part where the constituent portion exists be set to have the same hardness as the body portion.

The catheter may have a configuration in which another constituent portion forming a part of the distal end portion other than a part where the constituent portion exists is softer than the constituent portion and harder than the body portion.

Alternatively, the catheter may have a configuration in which another constituent portion forming a part of the distal end portion other than a part where the constituent portion exists is softer than the body portion.

According to another embodiment, a catheter assembly includes: a catheter having a distal end portion and a body portion that is continuous with a proximal end of the distal end portion and extends along an axial direction; a hollow inner needle that has a needle tip and is removably inserted into the catheter; and a guide wire that is inserted into the inner needle so as to be movable back and forth and is delivered from the needle tip, the distal end portion of the catheter having a constituent portion that has higher slipperiness than the body portion on at least a part of a surface of the distal end portion.

In this case, the catheter may have a configuration in which another constituent portion forming a part of the distal end portion other than a part where the constituent portion exists has lower slipperiness than the constituent portion and higher slipperiness than the body portion.

Alternatively, the catheter may have a configuration in which another constituent portion forming a part of the distal end portion other than a part where the constituent portion exists has lower slipperiness than the body portion.

According to another embodiment, a catheter assembly includes: a catheter having a distal end portion and a body portion that is continuous with a proximal end of the distal end portion and extends along an axial direction; a hollow inner needle that has a needle tip and is removably inserted into the catheter; and a guide wire that is inserted into the inner needle so as to be movable back and forth and is delivered from the needle tip, the distal end portion of the catheter having a constituent portion that has higher restorability than the body portion on at least a part of a surface of the distal end portion.

In this case, the catheter may have a configuration in which another constituent portion forming a part of the distal end portion other than a part where the constituent portion exists has lower restorability than the constituent portion and higher restorability than the body portion.

Alternatively, the catheter may have a configuration in which another constituent portion forming a part of the distal end portion other than a part where the constituent portion exists has lower restorability than the body portion.

According to certain embodiments of the present invention, the catheter assembly has the constituent portion harder than the body portion on at least a part of the surface of the distal end portion of the catheter, and thus, can favorably suppress the damage to the catheter caused by the guide wire when the guide wire is delivered from the needle tip. That is, the distal end portion of the catheter has the hard constituent portion, and thus, can suppress at least one of piercing and scratching at the time of delivering the guide wire, and flipping at the time of moving the catheter. As a result, it is possible to cause the catheter to be easily movable, and to reduce problems such as damage to a blood vessel wall and obstruction of blood flow caused by the distal end portion of the damaged catheter when the catheter is moved or indwelled.

Further, according to certain embodiment, the catheter assembly has the constituent portion that has higher slipperiness than the body portion on at least a part of the surface of the distal end portion of the catheter, and thus, can favorably suppress the damage to the catheter caused by the guide wire when the guide wire is delivered from the needle tip. That is, the distal end portion of the catheter has the constituent portion with favorable slipperiness, and thus, it is possible to suppress at least one of piercing and scratching at the time of delivering the guide wire, and flipping at the time of moving the catheter, and it is possible to reduce problems such as damage to the blood vessel wall and obstruction of blood flow caused by the distal end portion of the damaged catheter.

Furthermore, in certain embodiments, the catheter assembly has the constituent portion that has higher restorability than the body portion on at least a part of the surface of the distal end portion of the catheter, and thus, can favorably suppress the damage to the catheter caused by the guide wire when the guide wire is delivered from the needle tip. That is, the distal end portion of the catheter has the constituent portion with favorable restorability, and thus, it is possible to suppress at least one of piercing and scratching at the time of delivering the guide wire, and flipping at the time of moving the catheter, and it is possible to reduce problems such as damage to the blood vessel wall and obstruction of blood flow caused by the distal end portion of the damaged catheter.

DETAILED DESCRIPTION

Hereinafter, embodiments of the present invention will be described in detail with reference to the accompanying drawings.

Figure 1:
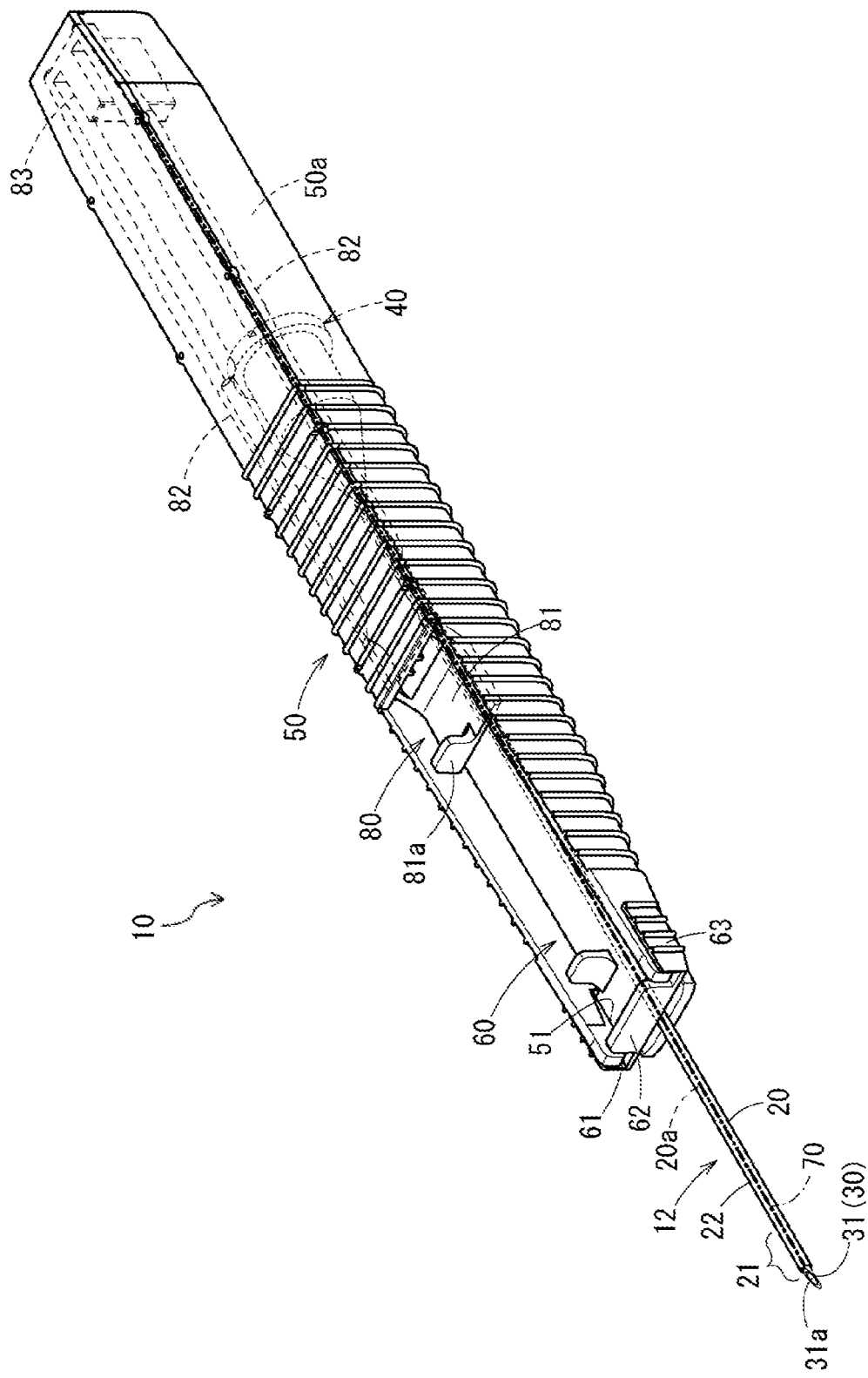
FIG. 1 is a perspective view illustrating an overall configuration of a catheter assembly according to an embodiment of the present invention.

A catheter assembly 10 according to one embodiment of the present invention includes a catheter 20 that is inserted from the outside of a body of a patient into the body and constructs an introducing section for infusion or blood transfusion in the patient (living body) using the catheter 20 as illustrated in FIG. 1. The catheter 20 may be one having a length longer than that of a peripheral venous catheter (for example, the catheter 20 may be a central venous catheter, a PICC, a mid-line catheter, and the like). Further, the catheter 20 may be configured as a peripheral venous catheter, or may be configured for an artery such as a peripheral artery catheter without being limited to the venous catheter.

In addition to the catheter 20, the catheter assembly 10 includes: an inner needle 30 that is removably inserted into the catheter 20; a catheter hub 40 that fixes and holds the catheter 20; and an inner needle hub 50 that fixes and holds the inner needle 30. Furthermore, the catheter assembly 10 includes: a catheter operating member 60 that operates the catheter 20 and the catheter hub 40; a guide wire 70 that is inserted into the inner needle 30 so as to be movable back and forth; and a guide wire operating member 80 that operates the guide wire 70.

Figure 2A:
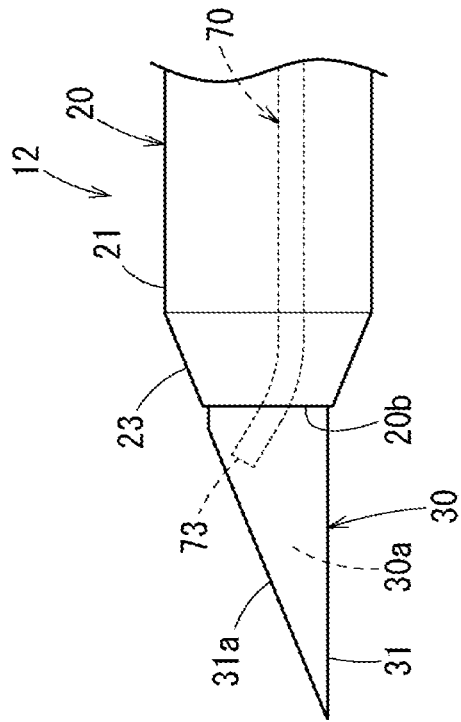
FIG. 2A is an enlarged side view illustrating a state in which a guide wire is accommodated in an inner needle.

The catheter assembly 10 constitutes a multi-structure needle 12 in which the catheter 20, the inner needle 30, and the guide wire 70 overlap with each other from the outside to the inside in a state before use (initial state) (see also FIG. 2A). Further, the catheter assembly 10 accommodates a proximal side of the multi-structure needle 12, the catheter hub 40, the catheter operating member 60, and the guide wire operating member 80 in the inner needle hub 50 in the initial state.

When using this catheter assembly 10, a user grasps the inner needle hub 50 to puncture the patient's blood vessel with a distal end of the multi-structure needle 12. Furthermore, the user operates the guide wire operating member 80 to advance relative to the inner needle hub 50 while maintaining the puncturing state, thereby delivering the guide wire 70 from the inner needle 30.

Figure 2B:
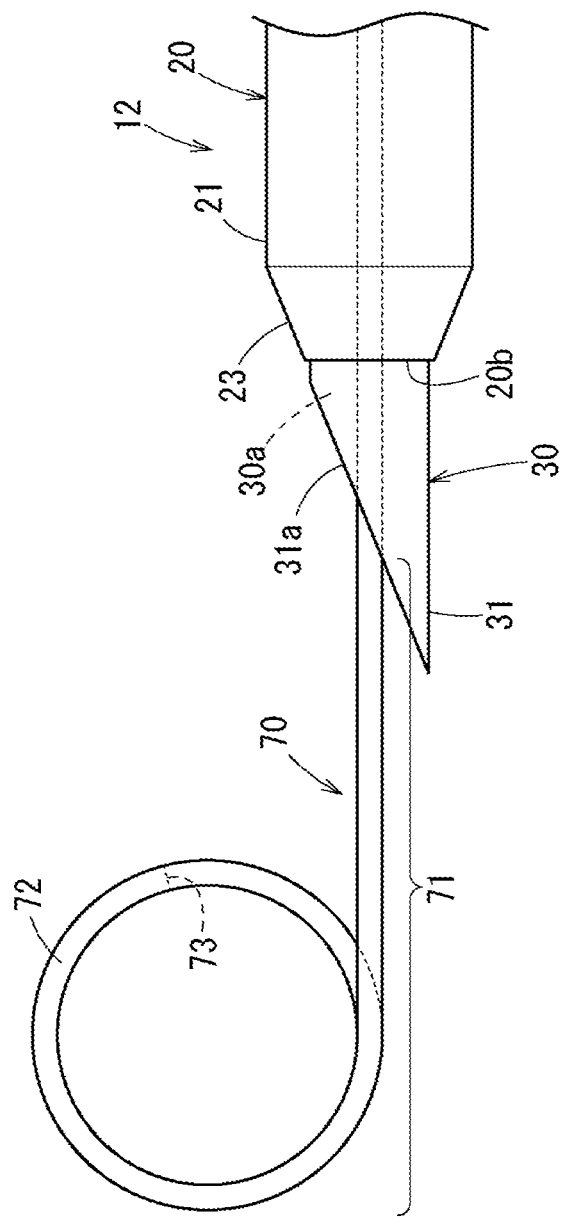
FIG. 2B is an enlarged side view illustrating a state in which the guide wire is delivered from the inner needle.

Here, when exposed from the inner needle 30, the guide wire 70 according to the present embodiment is deformed into a curved shape (hereinafter, referred to as a curved portion 72) as a distal portion of a delivered region 71 is wound in a coil shape as illustrated in FIG. 2B. The curved portion 72 is curved in an upward direction facing a blade surface to have a circular outer shape larger than a diameter of the catheter 20 in side view. The curved portion 72 is pre-shaped in a natural state in which the guide wire 70 is not accommodated in the inner needle 30, and is elastically deformed in a substantially linear shape when accommodated in the inner needle 30 (see also FIG. 3A). Therefore, when the guide wire 70 is exposed from the inner needle 30, the curved portion 72 immediately elastically restores and acts to return to the coil shape.

The catheter assembly 10 delivers the guide wire 70 having the curved portion 72, and thus, can insert the guide wire 70 without causing the distal end of the guide wire 70 to be caught on a blood vessel wall and without damaging the blood vessel wall. The curved portion 72 of the guide wire 70 is inserted deep inside the blood vessel under the operation of the user. Thereafter, the user advances the catheter operating member 60 relative to the inner needle hub 50, thereby advancing the catheter 20 and the catheter hub 40 to the distal side of the inner needle 30. At this time, the catheter 20 is inserted into the blood vessel along the preceding guide wire 70.

Then, the catheter 20 and the catheter hub 40 are advanced relative to the inner needle 30 and the inner needle hub 50 (or the inner needle 30 and the inner needle hub 50 are retracted relative to the catheter 20 and the catheter hub 40) so that the catheter hub 40 is detached from the inner needle 30. Thereafter, the catheter operating member 60 is removed from the catheter hub 40 so that the catheter 20 and the catheter hub 40 are indwelled on the patient side. Hereinafter, the catheter assembly 10 will be specifically described.

The catheter 20 of the catheter assembly 10 is formed as a tubular member having a distal end portion 21 and a body portion 22 that is continuous with the distal end portion 21 and extends in the axial direction as illustrated in FIGS. 1, 2A, and 2B. The catheter 20 is formed to have appropriate flexibility, and has an axially extending inner cavity 20a therein. The inner cavity 20a communicates with a distal opening 20b provided at a distal end of the catheter 20. A total length of the catheter 20 is not particularly limited, but may be, for example, 14 to 500 mm, preferably 30 to 400 mm, and more preferably 76 to 200 mm.

Further, the distal end portion 21 of the catheter 20 according to the present embodiment has a tapered outer peripheral surface 23 that tapers in the distal direction. Furthermore, the distal end portion 21 is designed to be harder than the body portion 22. A configuration of the distal end portion 21 of the catheter 20 will be described in detail below.

On the other hand, a proximal end portion of the catheter 20 is fixed to a distal end portion in the catheter hub 40 by an appropriate fixing means such as caulking, fusion, adhesion, and insert molding. The catheter hub 40 has a tubular shape that tapers in the distal direction, and has an internal space (not illustrated) that communicates with the inner cavity 20a of the catheter 20 therein. The catheter hub 40 is exposed on the patient's skin in a state in which the catheter 20 is inserted into the patient's blood vessel, and is connected to another medical device (a tube for infusion or blood transfusion).

A constituent material of the catheter hub 40 is not particularly limited, but a thermoplastic resin, such as polypropylene, polycarbonate, polyamide, polysulfone, polyarylate, and a methacrylate-butylene-styrene copolymer may be preferably used.

The inner needle 30 of the catheter assembly 10 is configured as a hollow tubular body having rigidity capable of puncturing a skin of a living body, and has a sharp needle tip 31 at a distal end thereof. A hollow portion 30a extending in the axial direction is provided inside the inner needle 30, and the hollow portion 30a communicates with a distal opening 31a provided at the needle tip 31.

Examples of a constituent material of the inner needle 30 include a metal material such as stainless steel, aluminum or an aluminum alloy, and titanium or a titanium alloy, a hard resin, ceramics, and the like. The inner needle 30 is firmly fixed to the inner needle hub 50 by an appropriate fixing means such as fusion, adhesion, and insert molding.

The inner needle hub 50 has an elongated rectangular tubular shape extending to be shorter than an axial length of the inner needle 30, and has an accommodation space 50a therein. A needle holding portion (not illustrated) that fixes a proximal end of the inner needle 30 at a predetermined height position is provided inside the accommodation space 50a.

Further, a predetermined range on the distal side of the inner needle hub 50 opens the accommodation space 50a upward, and distal portions of the catheter operating member 60 and the guide wire operating member 80 are arranged therein. Furthermore, a pair of rail portions 51 that are arranged to be slidable on side edges of the catheter operating member 60 are provided on inner side surfaces of the inner needle hub 50. A resin material forming the inner needle hub 50 is not particularly limited, but, for example, the materials exemplified for the catheter hub 40 can be appropriately selected.

The catheter operating member 60 is formed in a flat plate shape, and the catheter hub 40 is attached to a proximal end portion of the catheter operating member 60 in the initial state. Then, the catheter operating member 60 extends from a predetermined position in the accommodation space 50a to the distal end in a state in which the side edge 61 is accommodated in the rail portion 51 of the inner needle hub 50. The catheter 20 (multi-structure needle 12) extends below the catheter operating member 60, and is supported between the inner needle hub 50 and the catheter operating member 60 such that vertical deflection is suppressed. At the distal end of the catheter operating member 60, an upper operating portion 62 and a lateral operating portion 63 configured for the user to operate the catheter operating member 60 are provided.

The proximal end portion of the catheter operating member 60 is configured, for example, such that engagement with the catheter hub 40 continues in a posture of sliding along the longitudinal direction of the inner needle hub 50 and the engagement with the catheter hub 40 is released when being inclined at a predetermined angle with respect to the catheter hub 40.

Further, the guide wire operating member 80 is arranged on an upper surface of the catheter operating member 60 in the initial state. The guide wire operating member 80 includes: an operation plate portion 81 on the distal side; a pair of extending portions 82 extending from the operation plate portion 81 in the proximal direction; and a holding body 83 bridging a gap between proximal ends of the pair of extending portions 82 to hold the guide wire 70.

The operation plate portion 81 has an operation protrusion 81a, configured for the user to operate the guide wire operating member 80, at a distal end. The pair of extending portions 82 are connected to both sides of the operation plate portion 81 on the proximal side. The pair of extending portions 82 extend from the operation plate portion 81 in the proximal direction, and the holding body 83 is arranged on the proximal side of the accommodation space 50a of the inner needle hub 50.

The holding body 83 is formed in a block having a rectangular shape that is long in the vertical direction, and is located in the middle of the pair of extending portions 82 in the width direction. The guide wire 70 is inserted from a distal end face of the holding body 83 and is fixed inside the holding body 83. The holding body 83 is arranged at a position facing the needle holding portion of the inner needle hub 50.

The guide wire 70 held by the holding body 83 extends inside the inner needle hub 50 in the distal direction (toward the needle holding portion) as illustrated in FIG. 1, and is inserted into the hollow portion 30a of the inner needle 30 fixed to the needle holding portion. The guide wire 70 is formed to have such a length that a distal end is located proximal of the distal opening 31a of the inner needle 30 in a state in which the holding body 83 is located on the proximal side inside the inner needle hub 50.

Then, the guide wire 70 receives a moving force at the time of the advancing operation of the guide wire operating member 80 performed by the user, and advances inside the inner needle 30 so that the distal end thereof is delivered from a needle tip 31. As described above, the delivered region 71 of the guide wire 70 forms the curved portion 72 in the coil shape when exposed from the needle tip 31.

Figure 3A:
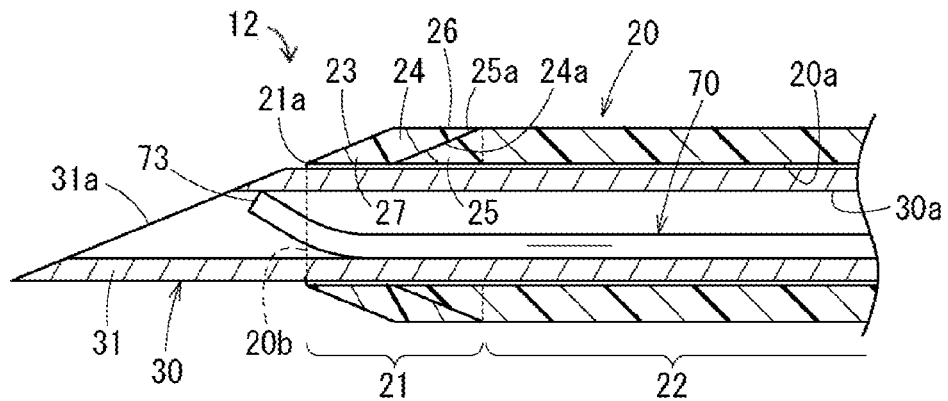
FIG. 3A is an enlarged side cross-sectional view illustrating the state in which the guide wire is accommodated in the inner needle.
Figure 3B:
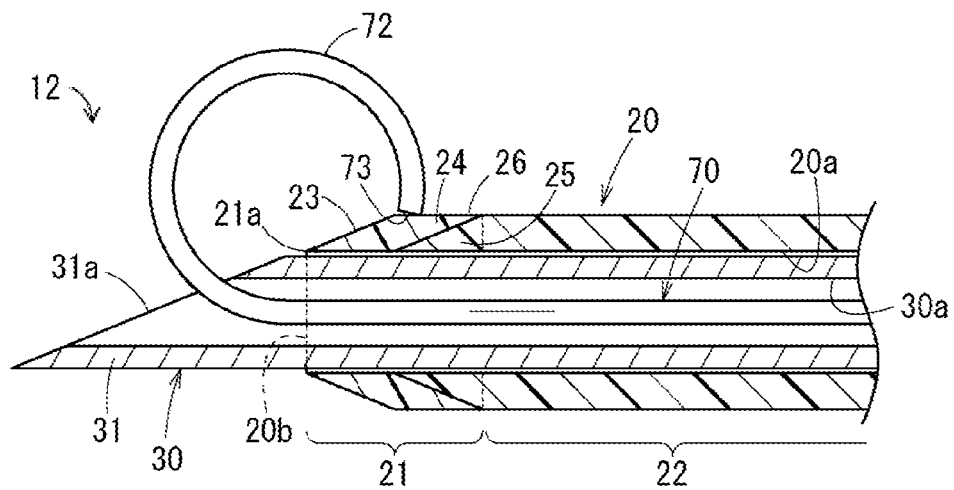
FIG. 3B is a side cross-sectional view illustrating an example of being in contact with a distal end portion of a catheter when the guide wire is delivered.

In the catheter assembly 10 having the guide wire 70 described above, a distal end 73 of the guide wire 70 is bent back toward the proximal side and the axial center of the multi-structure needle 12 due to the curving when elastically restored, and thus, sometimes come into contact with an outer peripheral surface of the distal end portion 21 of the catheter 20, for example, as illustrated in FIG. 3B at the initial stage of delivery of the guide wire 70 from the needle tip 31 of the inner needle 30. Further, in the catheter assembly 10, a most distal end 21a (a part of the distal end portion 21) of the catheter 20 comes into contact with the curved portion 72, for example, as illustrated in FIG. 3C when the catheter 20 is advanced along the guide wire 70.

Here, the "distal end portion 21" of the catheter 20 in the present specification indicates a range of a predetermined length (a dimension longer than an outer diameter of the curved portion 72 of the guide wire 70) from the most distal end 21a of the catheter 20 toward the proximal side. For example, an axial length of the distal end portion 21 is designed to be ⅒ or less of an axial length of the body portion 22. Then, the distal end portion 21 of the catheter 20 according to the present embodiment is the range including a portion where the tapered outer peripheral surface 23 is formed and a portion that is slightly proximal of the tapered outer peripheral surface 23.

Figure 3C:
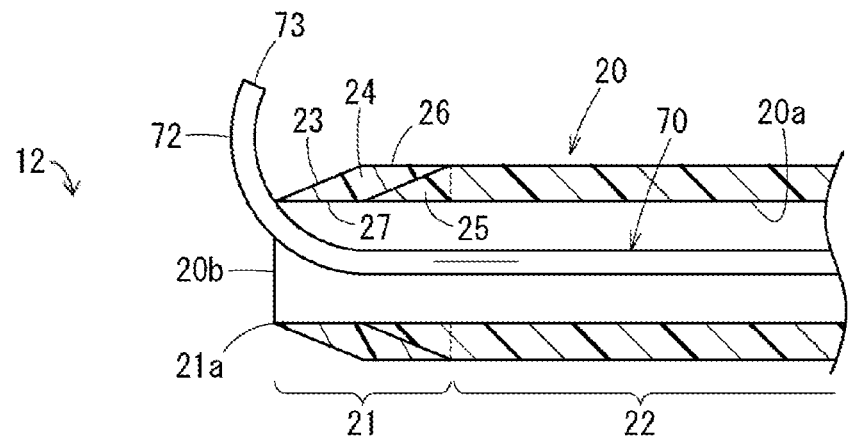
FIG. 3C is a side cross-sectional view illustrating an example of being in contact with the distal end portion of the catheter when the catheter is moved along the guide wire.

Further, the distal end portion 21 of the catheter 20 is formed to be harder than the body portion 22 of the catheter 20 in order to support the operation of the guide wire 70 as illustrated in FIGS. 3B and 3C. Specifically, the distal end portion 21 of the catheter 20 includes a first constituent portion 24 (constituent portion) made of a material different from that of the body portion 22 and a second constituent portion 25 (another constituent portion) made of the same material as the body portion 22.

The first constituent portion 24 is a portion that includes the most distal end 21a of the catheter 20 and forms the most distal side of the distal end portion 21 of the catheter 20. An outer peripheral surface of the first constituent portion 24 has the tapered outer peripheral surface 23 and a parallel outer peripheral surface 26 that is continuous with the tapered outer peripheral surface 23 and extends parallel to the axial center of the catheter 20. The parallel outer peripheral surface 26 is flush and continuous with the outer peripheral surface of the body portion 22. Further, an inner peripheral surface of the first constituent portion 24 is a parallel inner peripheral surface 27 extending parallel to the axial center of the catheter 20 from the most distal end. A proximal end face 24a of the first constituent portion 24 connects proximal ends of the parallel outer peripheral surface 26 and the parallel inner peripheral surface 27, and is inclined inward in the distal direction.

The first constituent portion 24 is provided on the entire circumference of the catheter 20 in the circumferential direction. Incidentally, the first constituent portion 24 may be provided partially in a direction in which the guide wire 70 is bent back by the curved portion 72 (at the upper position in FIG. 3B) as well as on the entire circumference of the catheter 20 in the circumferential direction.

The second constituent portion 25 forms a part of the distal end portion 21 other than a part where the first constituent portion 24 exists, and is connected to the proximal end face 24a of the first constituent portion 24 to form the inside of the distal end portion 21 in FIG. 3A. A distal end face 25a of the second constituent portion 25 is formed in a tapered shape corresponding to the proximal end face 24a of the first constituent portion 24. Since the second constituent portion 25 is made of the same material as the body portion 22, it can also be said that the body portion 22 is a portion formed to be tapered in the distal direction.

A constituent material of the body portion 22 and the second constituent portion 25 is not particularly limited, but a soft resin material is suitable, and examples thereof include a fluorine-based resin such as polytetrafluoroethylene (PTFE), ethylene-tetrafluoroethylene copolymer (ETFE) and perfluoroalkoxy fluorine resin (PFA), an olefin-based resin such as polyethylene and polypropylene or a mixture thereof, polyurethane, polyester, polyamide, polyether nylon resin, a mixture of the olefin-based resin and ethylene-vinyl acetate copolymer, and the like.

On the other hand, an appropriate material (a material harder than the body portion 22) may be selected as a constituent material of the first constituent portion 24 in response to the body portion 22, and the above materials may be applied. The hardness, or slipperiness or a restoring force, which will be described later, of the first constituent portion 24 is affected by the density of a material, a ratio of a mixture, and the like, and thus, the first constituent portion 24 may be made of the same material as the body portion 22.

The catheter 20 described above can be manufactured by molding the body portion 22 including the second constituent portion 25 in series, separately molding the first constituent portion 24, and bonding the first constituent portion 24 to the distal end face 25a of the second constituent portion 25 in the subsequent post-processing. Since the first constituent portion 24 and the second constituent portion 25 are bonded in a tapered shape, a bonding range is widened, and changes in physical properties of the catheter 20 in the axial direction are moderated.

Further, the distal end portion 21 of the catheter 20 has the first constituent portion 24, and thus, is configured to have physical properties of suppressing damage to the catheter 20 caused by the guide wire 70 (piercing of the distal end 73 of the guide wire 70, scratching by the distal end 73 of the guide wire 70, and the like) when the guide wire 70 is delivered from the inner needle 30 and is bent back. The physical properties in this case include the hardness of the catheter 20 itself, the slipperiness (lubricity) that causes sliding of the guide wire 70, and the restoring force (elasticity) when the guide wire 70 comes into contact.

Specifically, the catheter 20 can be set to have a relationship of Ha>Hb when a hardness Ha of the first constituent portion 24 and a hardness Hb of the body portion 22 are compared. Further, the catheter 20 can be set to have a relationship of Sa>Sb when a slipperiness Sa of the first constituent portion 24 and a slipperiness Sb of the body portion 22 are compared. Furthermore, the catheter 20 can be set to have a relationship of Ra>Rb when a restoring force Ra of the first constituent portion 24 and a restoring force Rb of the body portion 22 are compared.

Preferably, between the first constituent portion 24 and the body portion 22, at least one of the hardness relationship (Ha>Hb), the slipperiness relationship (Sa>Sb), and the restoring force relationship (Ra>Rb) is established. More preferably, two or more relationships are established, and even more preferably, all the three relationships are established.

That is, as illustrated in FIG. 3B, when the distal end 73 of the guide wire 70 comes into contact with the distal end portion 21 (first constituent portion 24) due to the elastic restoration of the curved portion 72, it is possible to suppress damage to the catheter 20 and allow the guide wire 70 to escape from the distal end portion 21 since the distal end portion 21 is hard in the catheter 20. As a result, the distal end 73 of the guide wire 70 is guided in the distal direction, and thus, can be smoothly restored into the coil shape. Similarly, the distal end portion 21 is slippery (has favorable slipperiness) in the catheter 20, and thus, it is possible to suppress damage to the catheter 20 and allow the guide wire 70 to escape from the distal end portion 21. Furthermore, the distal end portion 21 is easily restored (has a favorable restoring force), and thus, the catheter 20 can be deformed according to the guide wire 70 and then restored after allowing the guide wire 70 to escape when the guide wire 70 comes into contact.

Further, even if the curved portion 72 comes into contact with the inside of the catheter 20 when the catheter 20 is moved along the guide wire 70 as illustrated in FIG. 3C, it is possible to suppress flipping from the inside of catheter 20 and to smoothly move the catheter 20, since the distal end portion 21 is hard. Similarly, since the distal end portion 21 of the catheter 20 is slippery, a contact portion of the guide wire 70 is easily displaced, and the flipping can be suppressed. Furthermore, the catheter 20 has the favorable restoring force at the distal end portion 21, and thus, can be easily restored even if the flipping occurs from the inside of the catheter 20 so that it is possible to smoothly move the catheter 20.

Incidentally, the distal end 73 of the guide wire 70 comes into contact with the surface (outer peripheral surface and inner peripheral surface) of the distal end portion 21 of the catheter 20 as being curved. Accordingly, it suffices that the catheter 20 has a configuration in which the physical property (the hardness, the slipperiness, or the restoring force) of at least a part of the surface of the distal end portion 21 is higher than the physical property of the body portion 22. In particular, when the surface of the distal end portion 21 of the catheter 20 is set to four regions (a most distal region 91, an outer peripheral surface intermediate region 92, an outer peripheral surface proximal region 93, and an inner peripheral surface region 94) in an enlarged side cross-sectional view illustrated in FIG. 4, it suffices that the physical property of any of these regions is higher than the physical property of the body portion 22.

Specifically, the most distal region 91 is a portion that is located at a most distal end of the distal end portion 21 of the catheter 20 and includes the most distal end 21a. For example, a proportion of the most distal region 91 in the axial length of the distal end portion 21 is ⅕ or less. The most distal region 91 corresponds to a part where the distal end of the guide wire 70 comes into contact and easily flips when the catheter 20 is advanced. Therefore, if the most distal region 91 is harder, more slippery, or more easily restored than the body portion 22, the flipping of the catheter 20 can be favorably suppressed or the catheter 20 can be easily restored after flipping even if the guide wire 70 comes into contact.

The outer peripheral surface intermediate region 92 is a portion that is continuous with a proximal end of the most distal region 91, extends over the tapered outer peripheral surface 23, and includes a distal portion of the parallel outer peripheral surface 26 to some extent. The outer peripheral surface intermediate region 92 particularly corresponds to a part where the catheter 20 is easily scratched due to contact with the distal end 73 when the guide wire 70 is curved. Therefore, if the outer peripheral surface intermediate region 92 is harder, more slippery, or more easily restored than the body portion 22, the scratching of the catheter 20 can be favorably suppressed even if the guide wire 70 comes into contact.

The outer peripheral surface proximal region 93 is a portion which is continuous with a proximal end of the outer peripheral surface intermediate region 92 and in which the parallel outer peripheral surface 26 extends to the proximal end of the distal end portion 21. The outer peripheral surface proximal region 93 particularly corresponds to a part where the catheter 20 is easily pierced due to contact with the distal end 73 when the guide wire 70 is curved. Therefore, if the outer peripheral surface proximal region 93 is harder, more slippery, or more easily restored than the body portion 22, the puncturing of the catheter 20 can be favorably suppressed even if the guide wire 70 comes into contact.

The inner peripheral surface region 94 is a portion that is continuous with the proximal end of the most distal region 91 and extends over the inner peripheral surface of the catheter 20 to the proximal end of the distal end portion 21. The inner peripheral surface region 94 corresponds to a part that easily flips due to contact with the distal end 73 of the guide wire 70 when the catheter 20 is advanced or when the guide wire 70 moves into the hollow portion 30a, which is similar to the most distal region 91. Therefore, if the inner peripheral surface region 94 is harder, more slippery, or more easily restored than the body portion 22, the flipping of the catheter 20 can be favorably suppressed or the guide wire 70 can be easily returned after being flipped even if the guide wire 70 comes into contact.

Figure 4:
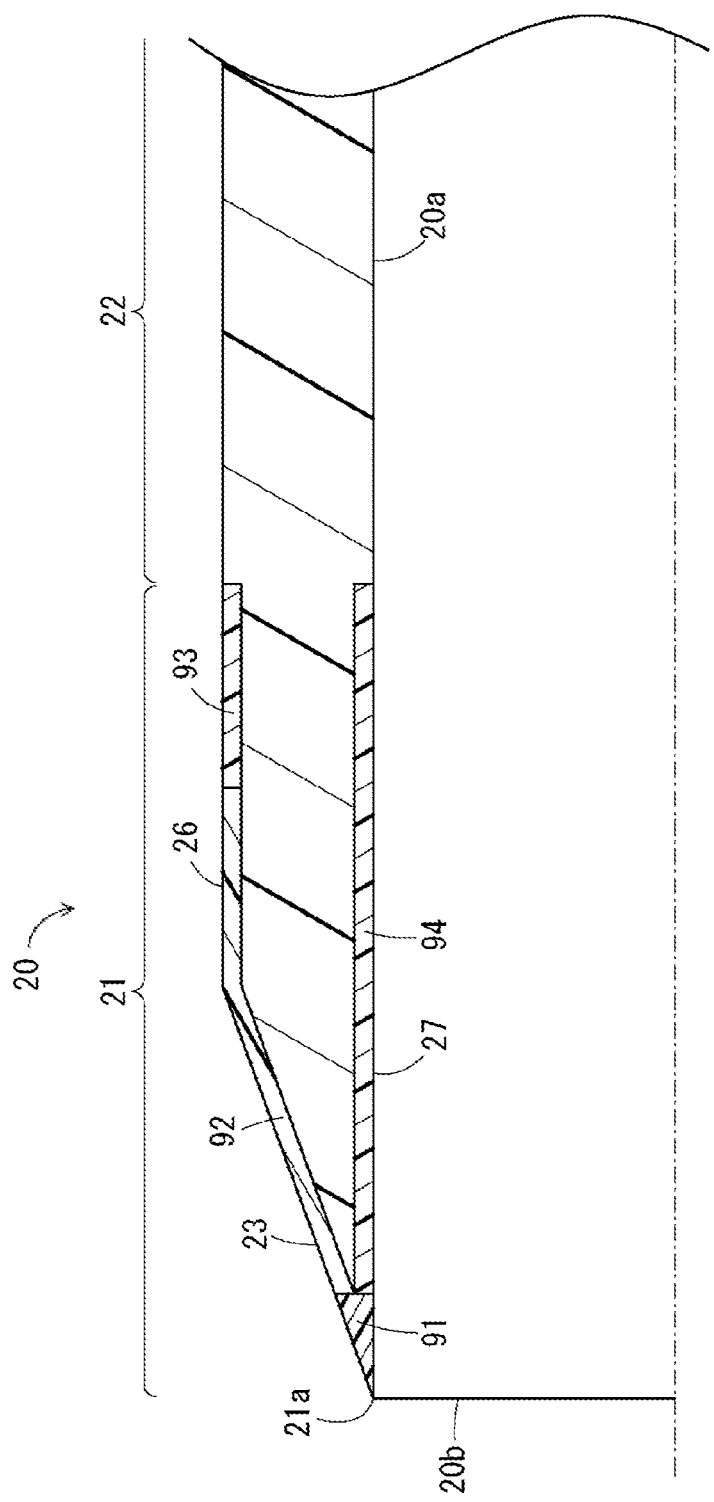
FIG. 4 is an enlarged side cross-sectional view illustrating a region of a surface of the distal end portion of the catheter.

That is, the catheter 20 of the catheter assembly 10 preferably adopts a configuration that enhances any of the physical property (the hardness, the slipperiness, or the restoring force) of any of the most distal region 91, the outer peripheral surface intermediate region 92, the outer peripheral surface proximal region 93, and the inner peripheral surface region 94 in FIG. 4. For example, in the distal end portion 21 of the catheter 20 in FIG. 3A described above, the first constituent portion 24 constitutes most of the distal end portion 21. Therefore, on the surface of the catheter 20, it is possible to enhance the physical properties of all the regions of the most distal region 91, the outer peripheral surface intermediate region 92, the outer peripheral surface proximal region 93 and the inner peripheral surface region 94 using the first constituent portion 24.

Figure 5A:
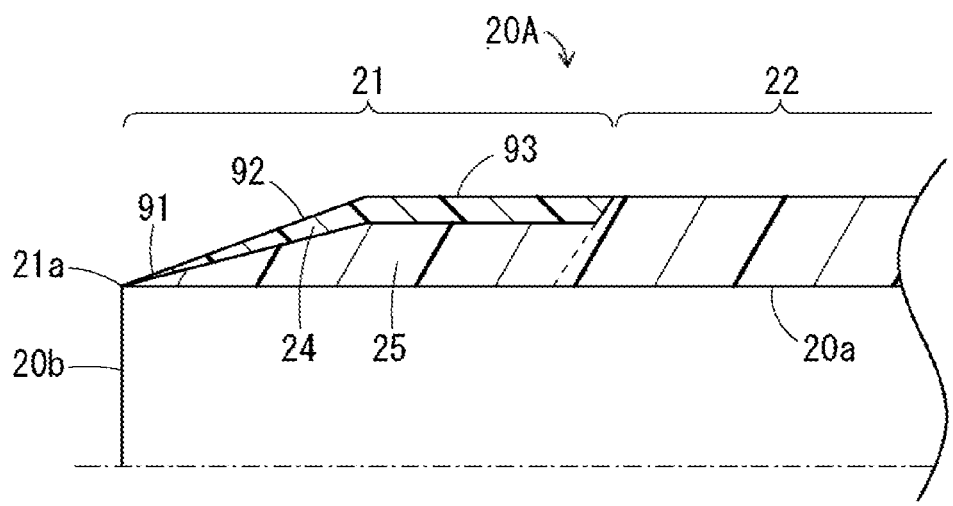
FIG. 5A is an enlarged side cross-sectional view illustrating a distal end portion of a catheter according to a first modification.

Further, as in a first modification illustrated in FIG. 5A, the distal end portion 21 of a catheter 20A may be configured such that the first constituent portion 24 is provided on the outside and the second constituent portion 25 is provided on the inside. Therefore, physical properties of the most distal region 91, the outer peripheral surface intermediate region 92, and the outer peripheral surface proximal region 93 are enhanced as compared to the body portion 22 on a surface of the distal end portion 21 of the catheter 20A using the first constituent portion 24.

That is, it is possible to favorably suppress piercing or scratching caused by the distal end 73 of the guide wire 70 since the distal end portion 21 of the catheter 20A is provided with the first constituent portion 24 on the outside. Further, the flexibility of the distal end portion 21 as a whole increases since the distal end portion 21 of the catheter 20A is provided with the second constituent portion 25 on the inside, and thus, it becomes easy to follow a meandering blood vessel. The catheter 20A can be manufactured by, for example, molding the first constituent portion 24 and the second constituent portion 25 in a stacked manner by extrusion molding and bonding the resultant to the body portion 22 by post-processing (each dotted line in FIGS. 5A and 5B indicates a bonding boundary portion between the distal end portion 21 and the body portion 22).

Figure 5B:
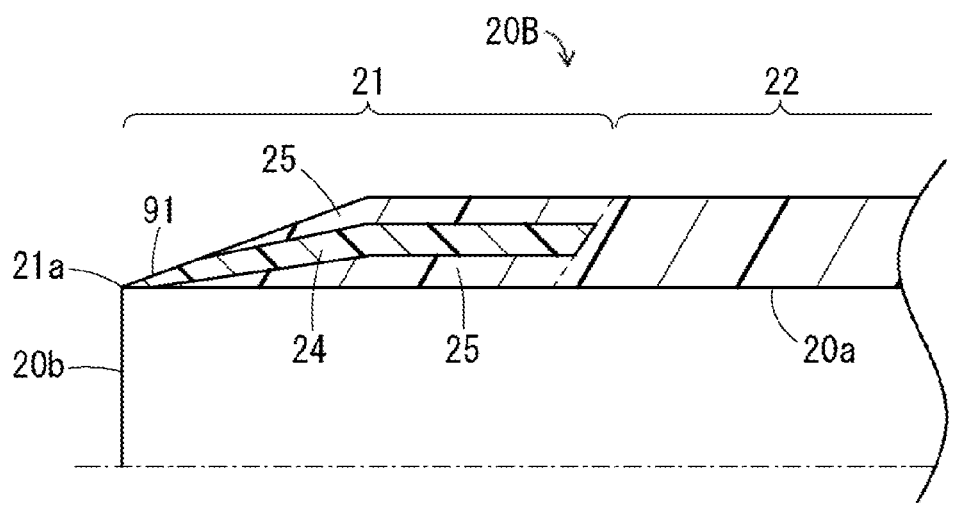
FIG. 5B is an enlarged side cross-sectional view illustrating a distal end portion of a catheter according to a second modification.

Furthermore, as in a second modification illustrated in FIG. 5B, the distal end portion 21 of a catheter 20B is configured to have a three-layer structure in which the first constituent portion 24 is provided in an intermediate layer and the second constituent portion 25 is provided in an inner layer and an outer layer. Further, the first constituent portion 24 is exposed to the outside in the most distal region 91. Therefore, a physical property of the most distal region 91 is enhanced as compared to the body portion 22 on a surface of the distal end portion 21 of the catheter 20B using the first constituent portion 24.

As a result, the distal end portion 21 of the catheter 20B can favorably suppress flipping when the catheter 20B is advanced along the guide wire 70. Further, the distal end portion 21 of the catheter 20B is provided with the second constituent portion 25 in the inner layer and the outer layer, and thus, can further enhance the flexibility of the distal end portion 21 as a whole as compared with the mode of the first modification. Further, the catheter 20B can also be manufactured by the same method as in the first modification.

Figure 6A:
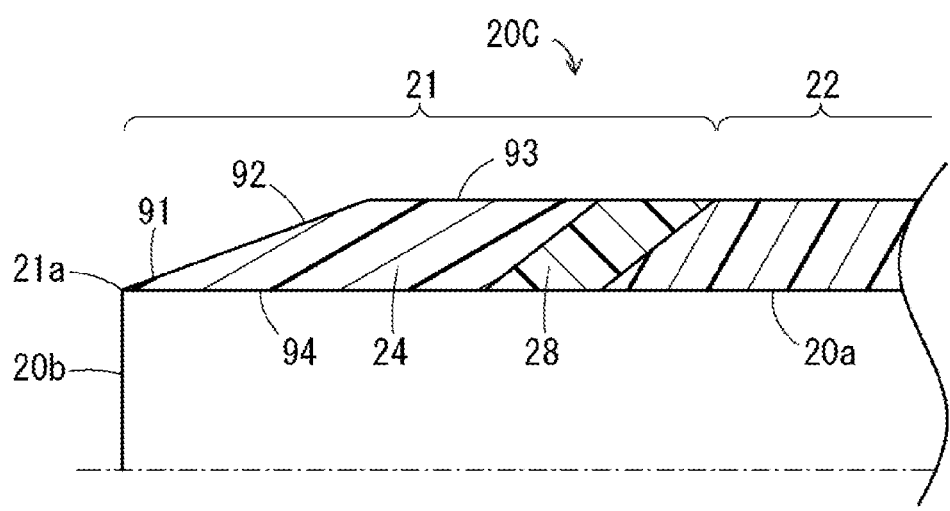
FIG. 6A is an enlarged side cross-sectional view illustrating a distal end portion of a catheter according to a third modification.

Furthermore, as in a third modification illustrated in FIG. 6A, the distal end portion 21 of a catheter 20C may have a configuration in which a second constituent portion 28 having a physical property different from those of the first constituent portion 24 and the body portion 22 is provided between the first constituent portion 24 and the body portion 22. The second constituent portion 28 is set to have a hardness Hc lower (softer) than the hardness Ha of the first constituent portion 24 and the hardness Hb of the body portion 22. That is, the hardness relationship in the catheter 20C is set such that Ha>Hb>Hc. As a result, the distal end portion 21 moves flexibly with respect to the body portion 22, and thus, it is possible to further enhance the followability to the blood vessel while piercing, scratching, and flipping of the distal end portion 21 (first constituent portion 24) caused by the distal end of the guide wire 70 are suppressed.

Incidentally, the hardness Hc of the second constituent portion 28 may be configured to be softer than the hardness Ha of the distal end portion 21 and harder than the hardness Hb of the body portion 22. That is, the hardness relationship in the catheter 20C may be set such that Ha>Hc>Hb. As a result, the catheter 20C is configured to gradually harden in the distal direction, so that it is possible to suppress generation of a kink caused by a change in physical property.

Further, the second constituent portion 28 may be configured such that another physical property such as a restoring force Rc is lower than a physical property of the first constituent portion 24. For example, if the restoring force relationship is set such that Ra>Rb>Rc or Ra>Rc>Rb in the catheter 20C, the distal end portion 21 can be favorably supported by the second constituent portion 28.

Figure 6B:
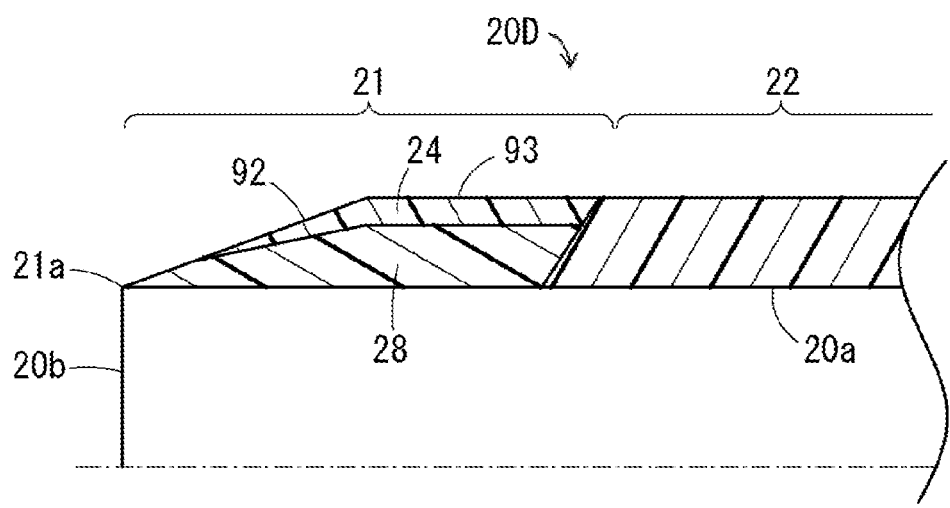
FIG. 6B is an enlarged side cross-sectional view illustrating a distal end portion of a catheter according to a fourth modification.

As in a fourth modification illustrated in FIG. 6B, a catheter 20D includes the first constituent portion 24 on the outside, and the second constituent portion 28 having a physical property different from those of the distal end portion 21 and the body portion 22 on the inside. That is, the second constituent portion 28 is configured to satisfy any relationship of Ha>Hb>Hc, Ha>Hc>Hb, Sa>Sb>Sc, Sa>Sc>Sb, Ra>Rb>Rc, and Ra>Rc>Rb when the hardness Hc, a slipperiness Sc, and the restoring force Rc are defined, which is similar to the third modification.

As a result, the distal end portion 21 of the catheter 20D can favorably suppress piercing or scratching caused by the distal end of the guide wire 70, and further, it is possible to design the entire distal end portion 21 to have a physical property that more easily follows a blood vessel.

That is, the catheters 20 and 20A to 20D are designed such that the first constituent portion 24 is arranged on at least a part of the surface of the distal end portion 21 and the relationship in the physical property (the hardness, the slipperiness, or the restoring force) among the first constituent portion 24, the second constituent portion 28, and the body portion 22 satisfies at least one or a plurality of the relationships among Ha>Hb>Hc, Ha>Hc>Hb, Sa>Sb>Sc, Sa>Sc>Sb, Ra>Rb>Rc, and Ra>Rc>Rb. As a result, the catheters 20 and 20A to 20D can suppress at least one of the piercing and scratching at the time of delivering the guide wire 70 and the flipping at the time of moving the catheters 20 and 20A to 20D.

Incidentally, the distal end portion 21 of the catheter 20 may be configured by performing coating in order to enhance the physical property of the surface (the most distal region 91, the outer peripheral surface intermediate region 92, the outer peripheral surface proximal region 93, and the inner peripheral surface region 94). A material used for the coating may be appropriately selected from materials that enhance the hardness, the slipperiness, or the restoring force by reacting with the material forming the catheter 20.

Figure 7A:
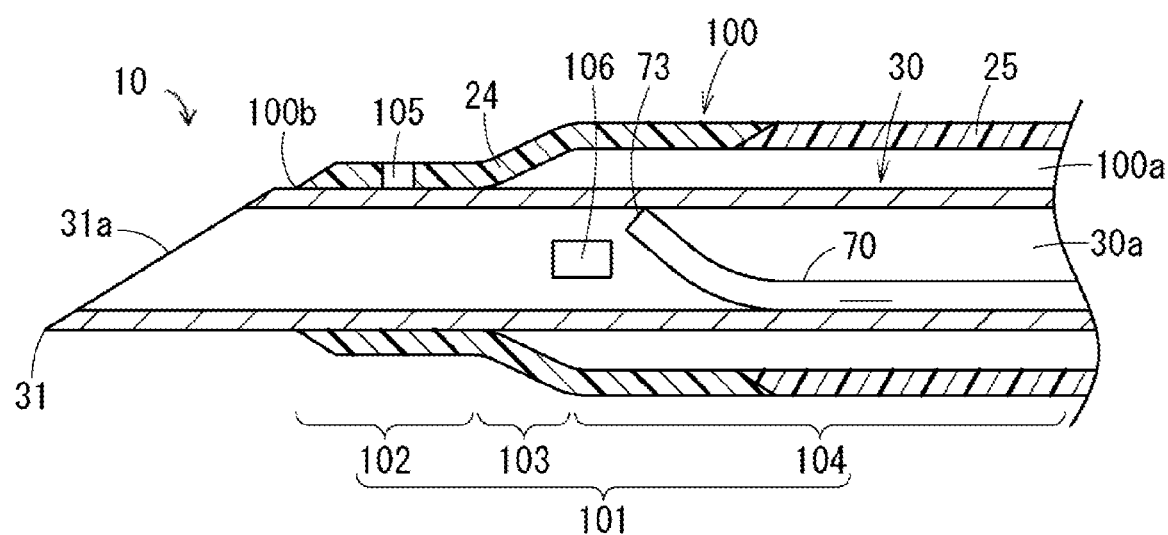
FIG. 7A is an enlarged side cross-sectional view illustrating a distal end portion of a catheter according to a fifth modification.

As in a fifth modification illustrated in FIG. 7A, a catheter 100 of the catheter assembly 10 may include: a distal contact portion 102 that is located at the most distal side and comes into contact (close-contact) with the outer peripheral surface of the inner needle 30; and a base portion 104 that is connected to a proximal end of the distal contact portion 102 via an inclined portion 103 and is separated from the inner needle 30. The distal contact portion 102, the inclined portion 103, and the base portion 104 constitute the same portion as the distal end portion 21 of the above-described catheter 20 (a distal end portion 101), and the proximal side of the base portion 104 is connected to the body portion 22. That is, the catheter 100 is closed by an inner peripheral surface of the distal contact portion 102 and the outer peripheral surface of the inner needle 30 at the distal contact portion 102 in the initial state, and has an inner cavity 100a which forms a space in the base portion 104 on the inside. The inner cavity 100a communicates with a distal opening 100b where the inner needle 30 is exposed.

The distal contact portion 102 is provided with a lateral opening 105 penetrating in the thickness direction of the catheter 100. That is, the lateral opening 105 is formed on the catheter 100 at a contact portion with the inner needle 30. The lateral opening 105 causes the inner cavity 100a to communicate with the outside of the distal contact portion 102 separately from the distal opening 100b. A formation position of the lateral opening 105 on the circumferential direction of the catheter 100 is not particularly limited, but is preferably located at the same position as a direction in which a blade surface of the needle tip 31 faces (upward in FIG. 7A), for example.

Further, the inner needle 30 has a side hole 106 (notch) at a position separated from the needle tip 31 (distal opening 31a) by a predetermined distance in the proximal direction. The side hole 106 is located at a position (non-contact portion with the catheter 100) overlapping with the inclined portion 103 or the base portion 104 in the initial state, and causes the inner cavity 100a closed by the distal contact portion 102 to communicate with the hollow portion 30a of the inner needle 30.

The distal end 73 of the guide wire 70 is arranged proximal of the side hole 106 in the initial state. Therefore, the inner needle 30 can smoothly guide blood flowing from the distal opening 31a into the hollow portion 30a to the inner cavity 100a through the side hole 106 when the needle tip 31 reaches a blood vessel, and the user can easily confirm the flashback of blood. A formation position of the side hole 106 on the circumferential direction of the inner needle 30 is not particularly limited, but is preferably provided in a direction different from the curving direction of the guide wire 70 shaped into the coil shape. For example, the side hole 106 is provided at a position that is displaced in phase by 90° with respect to the direction in which the blade surface of the needle tip 31 faces.

Further, the distal end portion 101 of the catheter 100 according to the fifth modification includes the first constituent portion 24 and the second constituent portion 25 made of the same material as that of the body portion 22 which is similar to the catheter 20 described above. The first constituent portion 24 extends over the distal contact portion 102, the inclined portion 103, and the distal side of the base portion 104. The second constituent portion 25 is provided on the proximal side of the base portion 104.

The first constituent portion 24 is made of a material harder than the second constituent portion 25 (or a material having higher slipperiness or a material having a higher restoring force). The catheter 100 configured as described above brings the distal end 73 of the guide wire 70 elastically restored into the coil shape into contact with the first constituent portion 24 when the guide wire 70 is delivered from the distal opening 31a of the inner needle 30. Therefore, the guide wire 70 can be released from the distal end portion 101 while the damage of the catheter 100 is suppressed.

Further, the catheter assembly 10 can guide blood into the inner cavity 100a of the catheter 100 in which the distal contact portion 102 is closed through the hollow portion 30a of the inner needle 30 and the side hole 106 at the time of puncturing using the multi-structure needle 12. At this time, since the lateral opening 105 exists in a part where the inner needle 30 and the catheter 100 are in contact with each other, no flashback blood is leaked. Therefore, it is possible to allow the user to favorably confirm the flashback of blood.

Furthermore, when the catheter 100 is indwelled in a blood vessel, the inner cavity 100a and the inside of the blood vessel communicate with each other through the two openings (the distal opening 100b and the lateral opening 105). Therefore, even if one opening (for example, the distal opening 100b) is closed by a blood vessel wall at the time of suctioning blood using the catheter 100, the other opening (for example, the lateral opening 105) is open so that the blood can be favorably suctioned.

Figure 7B:
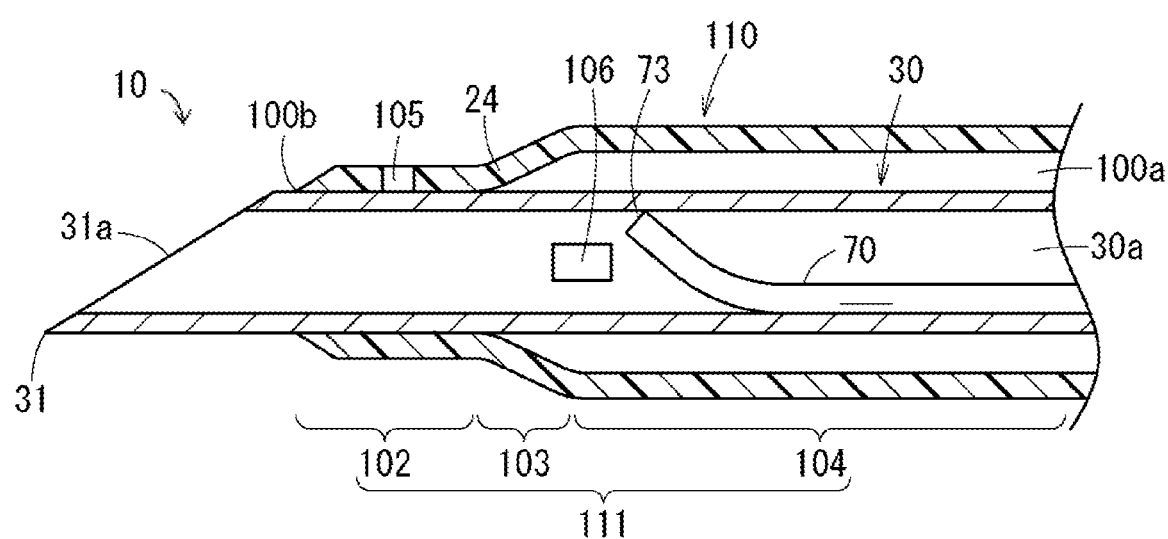
FIG. 7B is an enlarged side cross-sectional view illustrating a distal end portion of a catheter according to another configuration example.

Further, the catheter assembly 10 may have a catheter 110 in which a distal end portion 111 is configured using one constituent portion (for example, the first constituent portion 24) as in another configuration example of the fifth modification illustrated in FIG. 7B. Incidentally, in the catheter 110, configurations of the distal contact portion 102, the inclined portion 103, the base portion 104, the lateral opening 105, the side hole 106, and the like are the same as those described in FIG. 7A. Even if the distal end portion 111 of the catheter 110 is configured using one constituent portion in this manner, the same effects as those of the catheter 100 can be obtained.

Incidentally, it is a matter of course that the configuration in which the catheter 100 or 110 is provided with the lateral opening 105 and the inner needle 30 is provided with the side hole 106 can be applied to other embodiments, and can be also applied to, for example, the catheter assembly 10 of a multi-lumen type which will be described later.

Figure 8A:
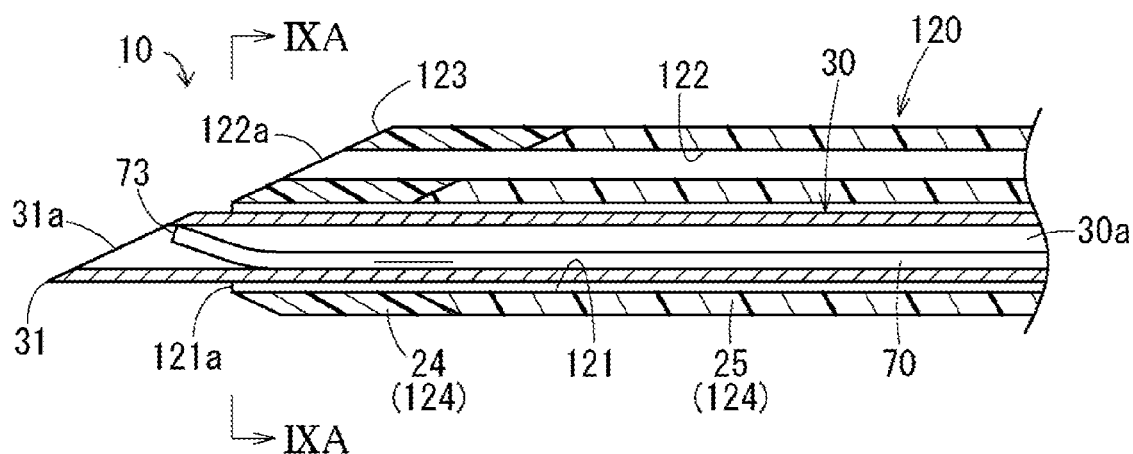
FIG. 8A is an enlarged side cross-sectional view illustrating a distal end portion of a catheter according to a sixth modification.
Figure 8B:
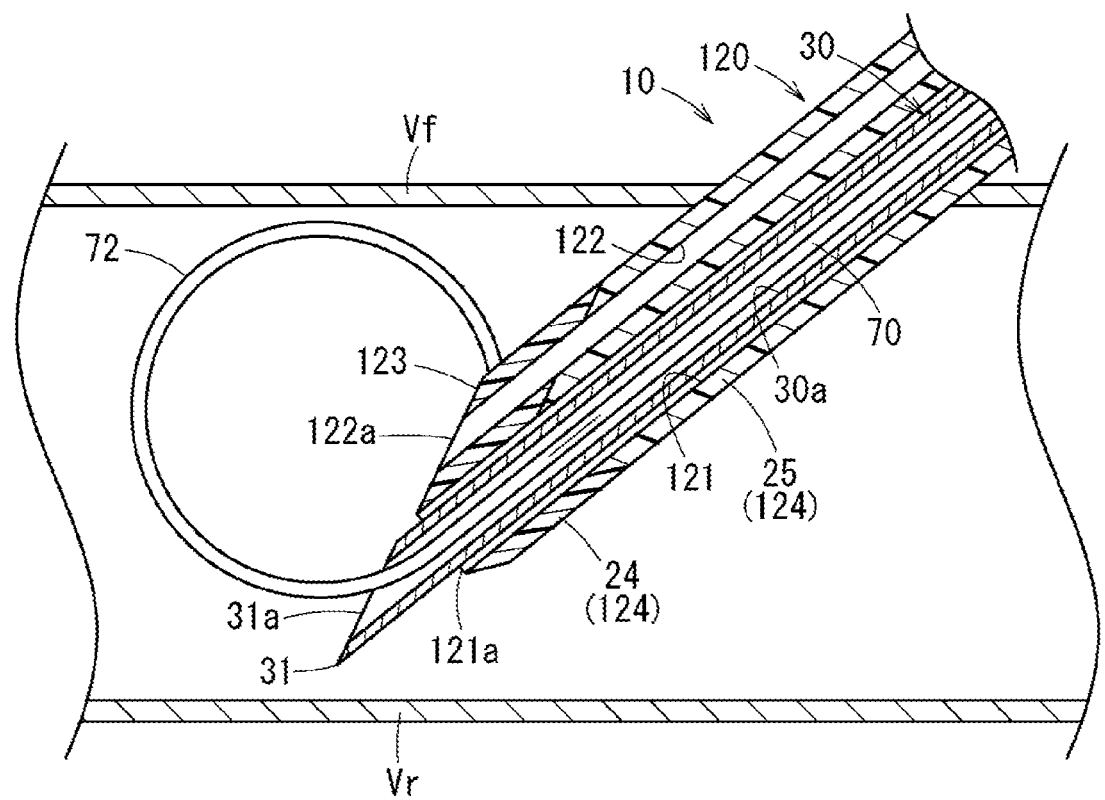
FIG. 8B is an enlarged side cross-sectional view illustrating a catheter assembly of FIG. 8A at the time of puncturing a blood vessel.
Figure 9A:
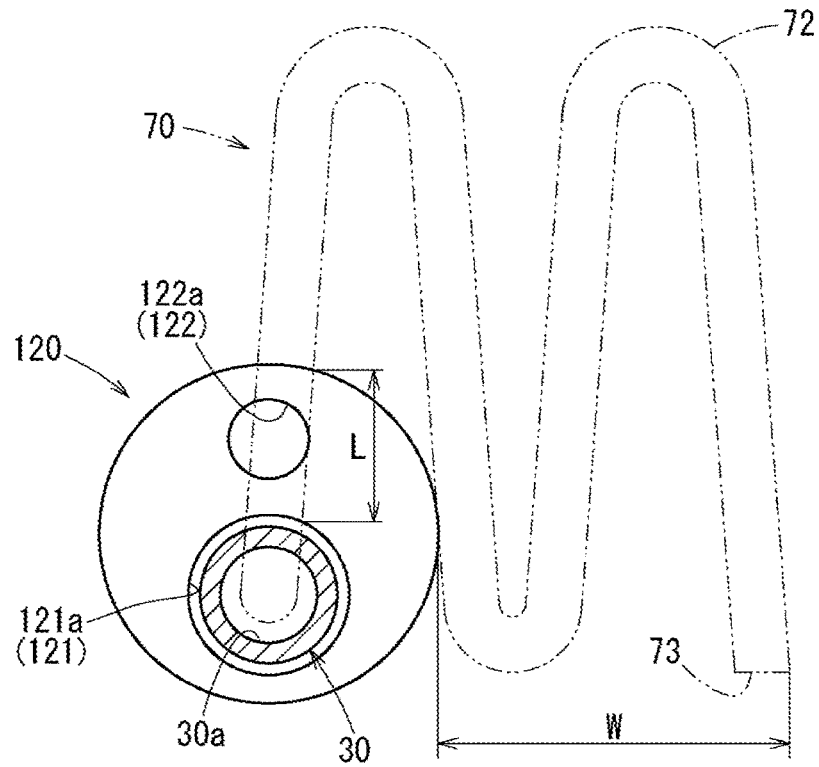
FIG. 9A is a cross-sectional view taken along line IXA-IXA of FIG. 8A.

A catheter 120 according to a sixth modification is configured as a double-lumen type (multi-lumen type) having two inner cavities (a main lumen 121 and a sub-lumen 122) as illustrated in FIGS. 8A, 8B, and 9A. Further, the inner needle 30 having the guide wire 70 arranged therein is inserted into the main lumen 121 in the catheter 120.

The main lumen 121 communicates with a distal opening 121a at the most distal end of the catheter 120. The needle tip 31 of the inner needle 30 is exposed from the distal opening 121a. The sub-lumen 122 is located on the upper side of the main lumen 121. Here, the "upper side" of the main lumen 121 refers to the same direction as the direction in which the blade surface of the needle tip 31 faces in the initial state. The "upper side" of the main lumen 121 also refers to a direction in which the guide wire 70 is bent back (curved) when the guide wire 70 shaped into the coil shape is elastically restored.

The sub-lumen 122 extends parallel to the main lumen 121 inside the catheter 120, and allows a liquid (a medicine solution or blood) different from that in the main lumen 121 to flow into a blood vessel. The distal opening 122a of the sub-lumen 122 is formed on a tapered surface 123 that is inclined obliquely in the proximal direction from a most distal end of the catheter 120, and is located to be slightly proximal of the distal opening 121a of the main lumen 121.

Further, a distal end portion 124 of the catheter 120 according to the sixth modification includes the first constituent portion 24 and the second constituent portion 25 made of the same material as that of the body portion 22 which is similar to the catheter 20 described above. In the illustrated example, the first constituent portion 24 and the second constituent portion 25 are provided on the entire circumference of the catheter 120 and a partition wall between the main lumen 121 and the sub-lumen 122, but the first constituent portion 24 may be partially provided on the upper side of the catheter 120 (in the periphery of the sub-lumen 122). The first constituent portion 24 is made of a material harder than the second constituent portion 25 (or a material having higher slipperiness or a material having a higher restoring force).

The catheter 120 configured as above can deliver the guide wire 70 from the distal opening 31a of the inner needle 30 arranged in the main lumen 121 at the time of puncturing using the multi-structure needle 12. As a result, the guide wire 70 shaped into the coil shape shifts to a wound around state inside a blood vessel.

At this time, the guide wire 70 is wound around at a position separated from a blood vessel front wall Vf in the catheter 120 in which the guide wire 70 is delivered from the main lumen 121 on the lower side (the inner needle 30) as illustrated in FIG. 8B, and thus, the interference from the guide wire 70 in the blood vessel front wall Vf is suppressed.

Further, as illustrated in FIG. 9A, the catheter 120 has an advantage that the catheter 120 is hardly damaged since a portion where a load is applied to the catheter 120 at the time of returning the guide wire 70 to the inner needle 30 is thick and a distance L is long. Furthermore, when the guide wire 70 is wound around a plurality of times to form the coil-shaped curved portion 72, the catheter 120 can make a pitch between the adjacent guide wires 70 dense (make a width W relatively narrow). Therefore, the curved portion 72 hardly damages a blood vessel rear wall Vr (FIG. 8B since the pressure applied to the blood vessel rear wall Vr is weak.

Figure 9B:
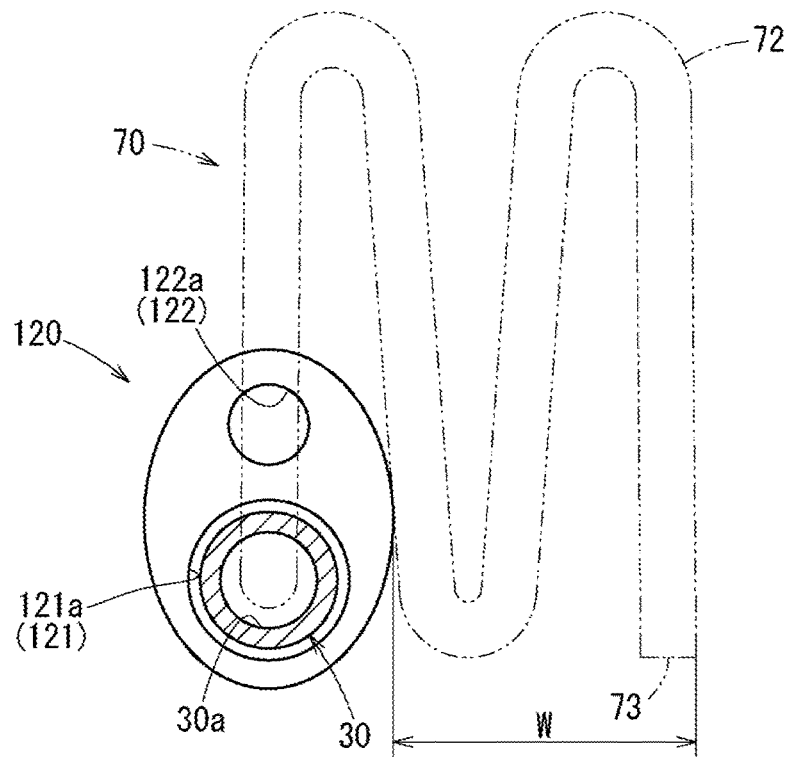
FIG. 9B is a front cross-sectional view illustrating a distal end portion of a catheter according to another configuration example.

Incidentally, the catheter 120 may be formed in an elliptical shape having a major axis in a direction in which the main lumen 121 and the sub-lumen 122 are arrayed in front view as in another configuration example of the sixth modification illustrated in FIG. 9B as well as formed in a perfect circular shape in front view as illustrated in FIG. 9A. The catheter 120 formed in the elliptical shape in this manner can narrow the width W (pitch between the adjacent guide wires 70) of the curved portion 72 of the guide wire 70, and can further weaken the pressure applied to the blood vessel rear wall Vr.

Figure 10A:
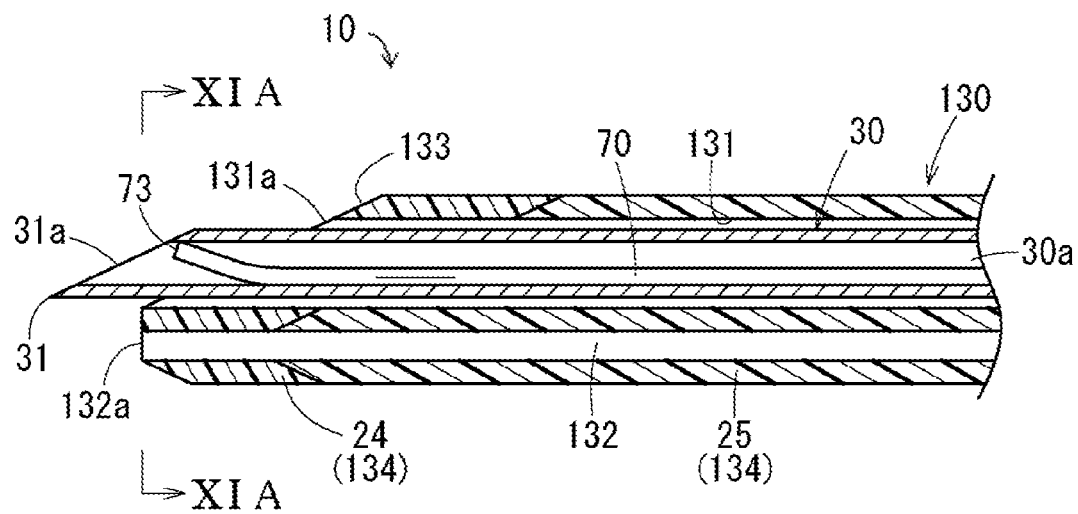
FIG. 10A is an enlarged side cross-sectional view illustrating a distal end portion of a catheter according to a seventh modification.
Figure 10B:
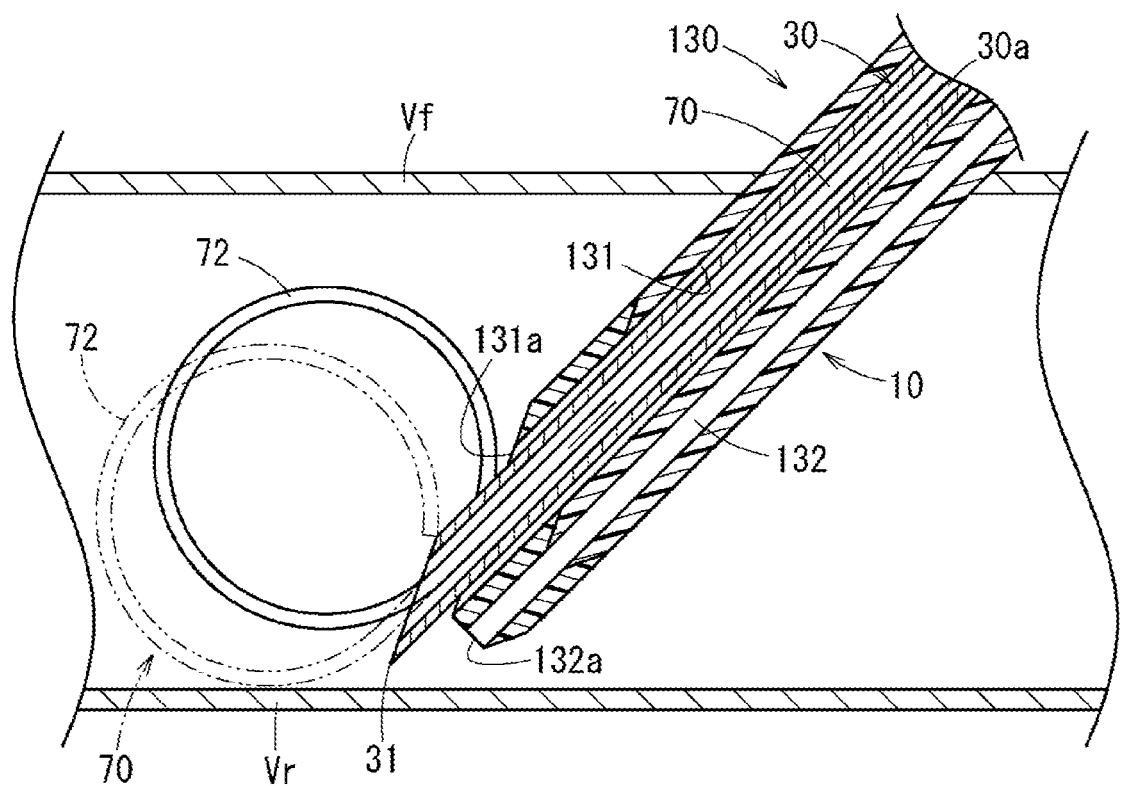
FIG. 10B is an enlarged side cross-sectional view illustrating a catheter assembly of FIG. 10A at the time of puncturing a blood vessel.
Figure 11A:
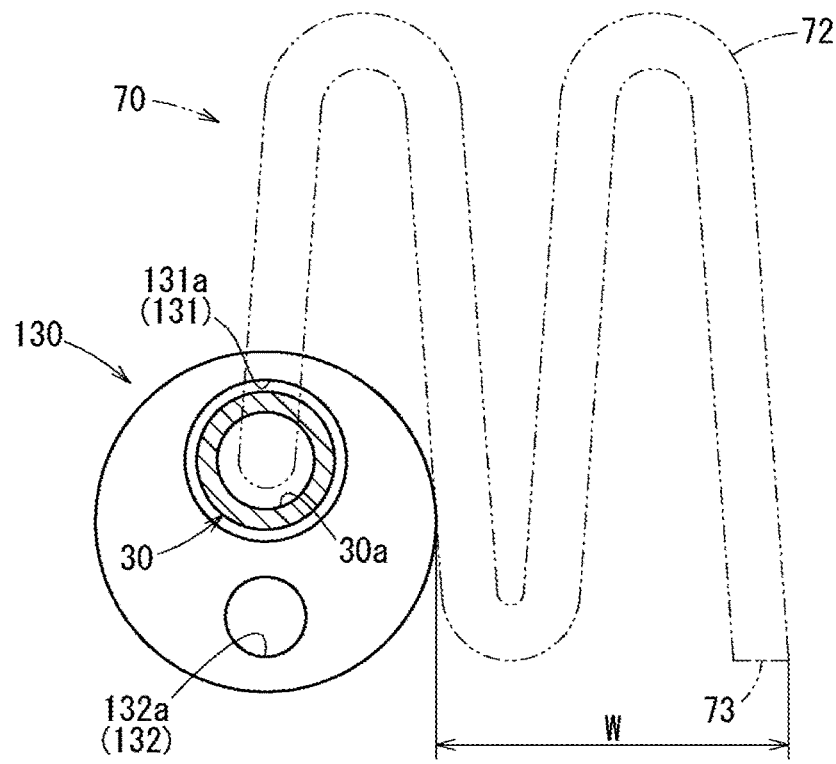
FIG. 11A is a cross-sectional view taken along line XIA-XIA of FIG. 10A.

A catheter 130 according to a seventh modification has a main lumen 131 and a sub-lumen 132 and a sub-lumen 132 as illustrated in FIGS. 10A, 10B, and 11A, but the sub-lumen 132 is located on the lower side of the main lumen 131. The inner needle 30 having the guide wire 70 arranged therein is inserted into the main lumen 131. The "lower side" of the main lumen 131 refers to a direction opposite to the direction in which the blade surface of the needle tip 31 faces in the initial state. Further, the "lower side" of the main lumen 131 corresponds to an opposite side with respect to a direction in which the curved portion 72 of the guide wire 70 shaped into the coil shape is formed.

For example, the sub-lumen 132 communicates with a distal opening 132a at the most distal end of the catheter 130. A distal opening 131a of the main lumen 131 is formed on a tapered surface 133 that is inclined obliquely in the proximal direction from a most distal end of the catheter 130, and is located to be slightly proximal of the distal opening 132a of the sub-lumen 132. In this case, the needle tip 31 of the inner needle 30 protrudes in the distal direction from the distal opening 131a.

Further, a distal end portion 134 of the catheter 130 according to the seventh modification also includes the first constituent portion 24 and the second constituent portion 25 made of the same material as that of the body portion 22 which is similar to the catheter 20 described above. The first constituent portion 24 is made of a material harder than the second constituent portion 25 (or a material having higher slipperiness or a material having a higher restoring force).

In the catheter 130 configured as above, the guide wire 70 has a long distance with respect to the blood vessel rear wall Vr (see the chain double-dashed line) as illustrated in FIG. 10B when the guide wire 70 is delivered from the main lumen 131 on the upper side (the inner needle 30). Therefore, the guide wire 70 is easily elastically deformed, and it is possible to suppress damage to the blood vessel rear wall Vr.

Figure 11B:
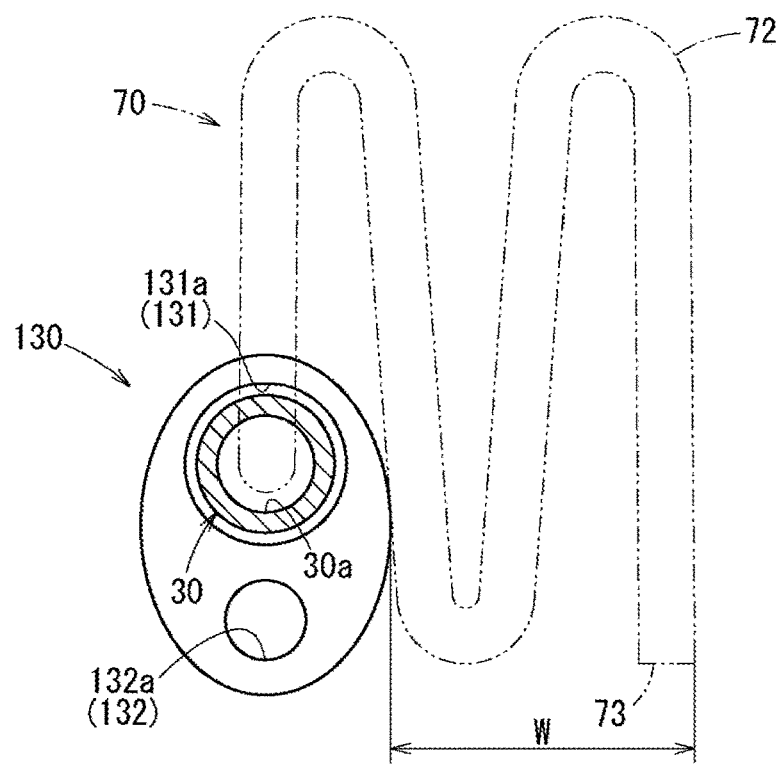
FIG. 11B is a front cross-sectional view illustrating a distal end portion of a catheter according to another configuration example.

Further, when the guide wire 70 is wound around a plurality of times to form the coil-shaped curved portion 72, the catheter 130 can make a pitch between the adjacent guide wires 70 dense (make a width W relatively narrow) as illustrated in FIG. 11A, which is similar to the catheter 120. Therefore, the curved portion 72 hardly damages a blood vessel rear wall Vr since the pressure applied to the blood vessel rear wall Vr is weak. Incidentally, the catheter 130 may be formed in an elliptical shape having a major axis in a direction in which the main lumen 131 and the sub-lumen 132 are arrayed in front view as in another configuration example of the seventh modification illustrated in FIG. 11B as well as formed in a perfect circular shape in front view as illustrated in FIG. 11A. The catheter 130 formed in the elliptical shape in this manner can also narrow the width W (pitch between the adjacent guide wires 70) of the curved portion 72 of the guide wire 70, and can further weaken the pressure applied to the blood vessel rear wall Vr.

Figure 12A:
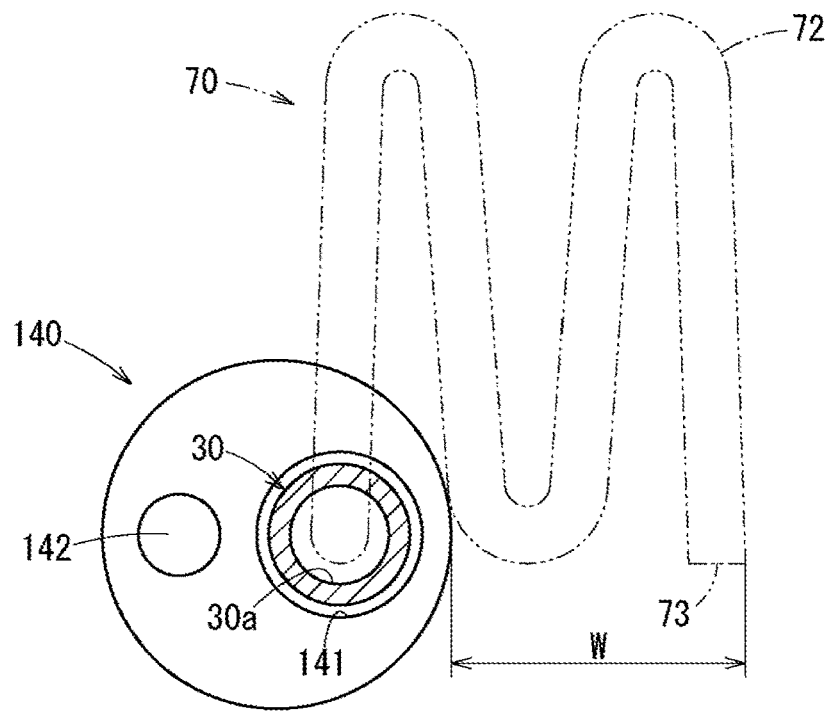
FIG. 12A is a front cross-sectional view illustrating a distal end portion of a catheter according to an eighth modification.

Further, when a catheter 140 is configured as a double-lumen type having a main lumen 141 and a sub-lumen 142 as in an eighth modification illustrated in FIG. 12A, the lumens of one another may be arranged side by side. Specifically, the catheter 140 has the sub-lumen 142 on the left side (in a first direction) of the main lumen 141 into which the inner needle 30 accommodating the guide wire 70 is inserted in front view. Here, the "left side" of the main lumen 141 refers to a direction opposite to a direction (right side: a second direction) in which the coil-shaped curved portion 72 is formed when the guide wire 70 is elastically restored.

The catheter 140 configured in this manner forms the curved portion 72 on the right side, which is separated from the sub-lumen 142, when the guide wire 70 is delivered from the main lumen 141. Therefore, it is possible to significantly narrow the width W (pitch between the adjacent guide wires 70) of the curved portion 72 of the guide wire 70, and to further weaken the pressure applied to the blood vessel rear wall Vr.

Figure 12B:
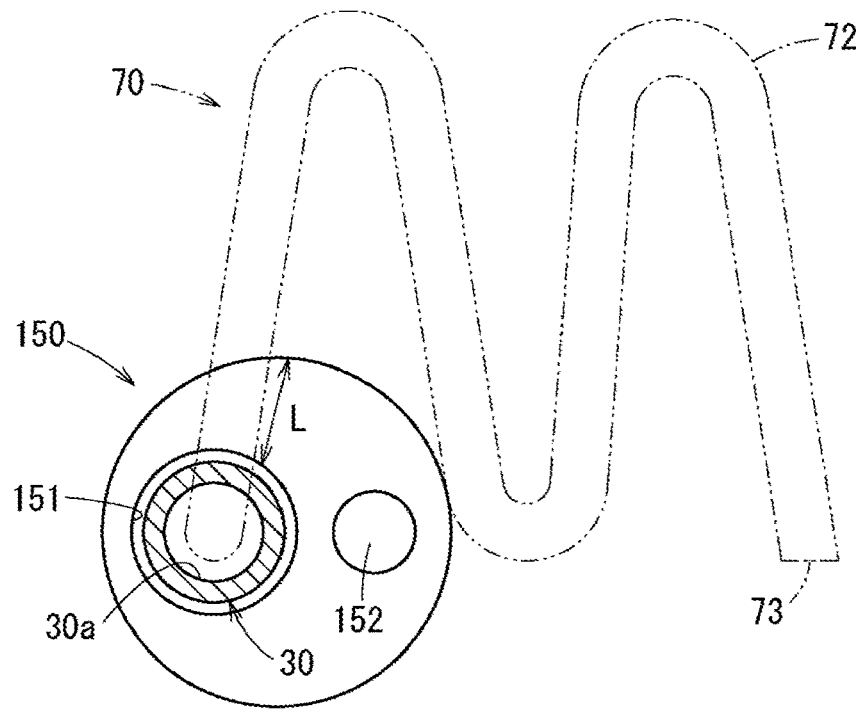
FIG. 12B is a front cross-sectional view illustrating a distal end portion of a catheter according to a ninth modification.

Furthermore, as in a ninth modification illustrated in FIG. 12B, a catheter 150 may be configured as a double lumen type having a sub-lumen 152 on the right side (in the second direction) of a main lumen 151 in front view. Here, the "right side" of the main lumen 151 refers to the same direction as the direction in which the coil-shaped curved portion 72 is formed when the guide wire 70 is elastically restored.

The catheter 150 configured in this manner has an advantage that the catheter 150 is hardly damaged since a portion where a load is applied to the catheter 150 at the time of returning the guide wire 70 to the inner needle 30 is thick and a distance L is long.

As described above, the catheter assembly 10 according to the present invention has the first constituent portion 24 that is harder than the body portion 22 on at least a part of the surface of the distal end portion 21 of the catheter 20. As a result, when the guide wire 70 is delivered from the needle tip 31 of the inner needle 30, the damage to the catheter 20 caused by the guide wire 70 can be favorably suppressed. That is, the distal end portion 21 of the catheter 20 has the hard first constituent portion 24, and thus, can suppress at least one of the piercing and scratching at the time of delivering the guide wire 70, and the flipping at the time of moving the catheter 20. As a result, it is possible to cause the catheter 20 to be easily movable, and to reduce problems such as damage to the blood vessel wall and obstruction of blood flow caused by the distal end portion 21 of the damaged catheter 20 when the catheter 20 is moved or indwelled.

Since the guide wire 70 has the curved portion 72 at the distal portion, the guide wire 70 can move inside the blood vessel while suppressing catching on or damage to the blood vessel wall. Further, the catheter 20 is configured with the hard distal end portion 21, damage is suppressed even if the curved portion 72 of the guide wire 70 comes into contact.

In particular, the catheter assembly 10 is provided with the first constituent portion 24 on the outer peripheral surface of the distal end portion 21 of the catheter 20, and thus, it is possible to suppress piercing or scratching of the catheter 20 and to allow the guide wire 70 to favorably escape when the distal end 73 of the guide wire 70 comes into contact with the outer peripheral surface.

In this case, the distal end portion 21 of the catheter 20 has the first constituent portion 24 on the tapered outer peripheral surface 23, and thus, can more reliably inhibit damage to a thin portion of the catheter 20 by inhibiting the guide wire 70 from scratching the tapered outer peripheral surface 23.

Further, the distal end portion 21 of the catheter 20 has the first constituent portion 24 on the outer peripheral surface (in the outer peripheral surface proximal region 93) on the proximal side of the tapered outer peripheral surface 23, and thus, can inhibit the distal end 73 of the guide wire 70 from piercing the catheter 20.

Furthermore, the distal end portion 21 of the catheter 20 has the first constituent portion 24 on the inner peripheral surface, and thus, the flipping of the catheter 20 can be suppressed even if the guide wire 70 comes into contact with the inner peripheral surface of the catheter 20 at the time of moving the catheter 20 with respect to the guide wire 70. Further, the damage to the inner peripheral surface caused by the distal end 73 of the guide wire 70 is also suppressed.

Further, the distal end portion 21 of the catheter 20 has the first constituent portion 24 at the most distal end 21a, and thus, can suppress the flipping of the most distal end 21a caused by the guide wire 70.

Furthermore, the distal end portion 21 of the catheter 20 has the second constituent portion 25 having the same hardness as the body portion 22 in addition to the first constituent portion 24, and thus, it is possible to suppress the influence of kink and the like caused when the hardness of the distal end portion 21 is greatly different from that of the body portion 22. Further, it is possible to form a favorable bonding state in the case of bonding the distal end portion 21 and the body portion 22 during the manufacture.

Alternatively, the distal end portion 21 of the catheter 20 has the second constituent portion 28 that is softer than the first constituent portion 24 and harder than the body portion 22 in addition to the first constituent portion 24, and thus, has a structure of being gradually harder in the distal direction of the catheter 20, so that it is possible to more reliably suppress the kink and the like.

Further, for example, the distal end portion 21 of the catheter 20 has the second constituent portion 28 that is softer than the body portion 22 in addition to the first constituent portion 24, and thus, it is possible to appropriately design the physical property of the distal end portion 21 and to cause the distal end portion 21 of the catheter 20 to easily follow the blood vessel.

The present invention is not limited to the above-described embodiments, and various modifications are possible that remain within the scope of the invention.

The invention claimed is:

1. A catheter assembly comprising:
   a catheter comprising a distal end portion, and a body portion that is continuous with a proximal end of the distal end portion and extends along an axial direction;
   a hollow inner needle that has a needle tip and is removably inserted into the catheter; and
   a guide wire that is inserted into the inner needle so as to be movable back and forth and that is deliverable from the needle tip,
   wherein the distal end portion of the catheter comprises, at an outer surface of the distal end portion, a constituent portion that is made of resin material and is harder than the body portion,
   wherein the guide wire is configured to curve upon exiting the inner needle such that a distal end tip of the guide wire hits the constituent portion, and
   wherein an axial length of the constituent portion of the catheter is greater than an outer diameter of a curved portion of the guide wire upon the guide wire exiting the inner needle.

2. The catheter assembly according to claim 1, wherein: the constituent portion is located at an outer peripheral surface of the distal end portion of the catheter.

3. The catheter assembly according to claim 2, wherein: the distal end portion of the catheter has a tapered outer peripheral surface that tapers in a distal direction, and the constituent portion is located in a region including the tapered outer peripheral surface.

4. The catheter assembly according to claim 2, wherein: the distal end portion of the catheter has a tapered outer peripheral surface that tapers in a distal direction, and the constituent portion is located proximal of the tapered outer peripheral surface.

5. The catheter assembly according to claim 1, wherein: the constituent portion extends to an inner peripheral surface of the distal end portion of the catheter.

6. The catheter assembly according to claim 1, wherein: the constituent portion is located at a most distal end of the distal end portion of the catheter.

7. The catheter assembly according to claim 1, wherein: the distal end portion of the catheter comprises a second constituent portion that has a hardness identical to a hardness of the body portion.

8. The catheter assembly according to claim 1, wherein:
the distal end portion of the catheter comprises a second constituent portion that is softer than the constituent portion and harder than the body portion.

9. The catheter assembly according to claim 1, wherein:
the distal end portion of the catheter comprises a second constituent portion that is softer than the body portion.

10. The catheter assembly according to claim 1, wherein:
in the catheter, a distal contact portion located on a most distal side in the distal end portion is in contact with the inner needle, and a portion proximal of the distal contact portion is separated from the inner needle,
the distal contact portion has a lateral opening penetrating in a thickness direction of the catheter, and
the inner needle has a side hole proximal of the distal contact portion.

11. The catheter assembly according to claim 1, wherein:
the catheter has a main lumen into which the inner needle is inserted, and a sub-lumen extending parallel to the main lumen.

12. The catheter assembly according to claim 1, wherein:
the distal end portion of the catheter comprises a second constituent portion that has a hardness identical to a hardness of the body portion; and
an interface between the constituent portion and the second constituent portion is tapered between an inner peripheral surface and an outer peripheral surface of the distal end portion of the catheter.

13. The catheter assembly according to claim 1, wherein:
an axial length of the distal end portion of the catheter is less than or equal to one-tenth of a length of the body portion of the catheter.

\* \* \* \* \*